(12) United States Patent
Ando et al.

(10) Patent No.: US 7,479,371 B2
(45) Date of Patent: Jan. 20, 2009

(54) METHOD OF JUDGING LEUKEMIA, PRE-LEUKEMIA OR ALEUKEMIC MALIGNANT BLOOD DISEASE AND DIAGNOSTIC THEREFOR

(75) Inventors: Kiyoshi Ando, Chigasaki (JP); Tomomitsu Hotta, Nagoya (JP); Chie Ito, Isehara (JP); Hidenao Sato, Tokyo (JP); Akiko Furuya, Tokyo (JP); Kenya Shitara, Tokyo (JP); Seiji Sugimoto, Tokyo (JP); Hiroaki Kohno, Sunto-gun (JP)

(73) Assignees: Tokai University, Tokyo (JP); Kyowa Hakko Kogyo Co., Ltd., Tokyo (JP); Kyowa Medex Co., Ltd., Tokyo (JP)

( * ) Notice: Subject to any disclaimer, the term of this patent is extended or adjusted under 35 U.S.C. 154(b) by 165 days.

(21) Appl. No.: 10/510,627

(22) PCT Filed: Apr. 9, 2003

(86) PCT No.: PCT/JP03/04531

§ 371 (c)(1),
(2), (4) Date: Jun. 20, 2005

(87) PCT Pub. No.: WO03/085399

PCT Pub. Date: Oct. 16, 2003

(65) Prior Publication Data

US 2006/0084122 A1 Apr. 20, 2006

(30) Foreign Application Priority Data

Apr. 9, 2002 (JP) .............................. 2002-106786

(51) Int. Cl.
*G01N 33/53* (2006.01)
*C07K 16/00* (2006.01)

(52) U.S. Cl. .................. 435/7.1; 530/387.9; 530/388.1

(58) Field of Classification Search ........................ None
See application file for complete search history.

(56) References Cited

U.S. PATENT DOCUMENTS

2002/0099196 A1 7/2002 Hiraoka et al.

FOREIGN PATENT DOCUMENTS

| EP | 0 880 447 A1 | 8/1998 |
|---|---|---|
| FR | 2771750 A1 | 6/1999 |
| WO | WO 98/08869 | 3/1998 |
| WO | WO 01/53500 A1 | 7/2001 |

OTHER PUBLICATIONS

International Preliminary Examination Report for PCT Application No. PCT/JP2003/004531, mailed Nov. 11, 2004.
Hiraoka et al., "Cloning, expression, and characterization of a cDNA encoding a novel human growth factor for primitive hematopoietic progenitor cells," *Proc. Natl. Acad. Sci.* USA, 94:7577-7582 (1997).
Hiraoka et al., "Stem cell growth factor: In situ hybridization anaylsis on the gene expression, molecular characterization and in vitro proliferative activity of a recombinant preparation on primitive hematopoietic progenitor cells," *Hematol J.*, 2(5):307-15 (2001).
Mio et al., "Isolation and characterization of a cDNA for human mouse, and rat full-length stem cell growth factor, a new member of C-type lectin superfamily," *Biochem Biophys Res Commun.*, 249(1):124-30 (1998).
Hiraoka et al., 1987, "Monoclonal antibodies against human hematopoietic survival and growth factor," *Biomed. Biochim. Acta*, 46(5): 419-427.
Hiraoka et al., 2001, "Stem cell growth factor: in situ hybridization analysis on the gene expression, molecular characterization and in vitro proliferative activity of a recombinant preparation on primitive hematopoietic progenitor cells," *The Hematology Journal*, 2: 307-315.
Ito et al., 2003, "Serum stem cell growth factor for monitoring hematopoietic recovery following stem cell transplantation," *Bone Marrow Transplantation*, 32: 391-398.
Supplementary European Search Report issued in EP App. No. 03 74 5988 dated May 30, 2007, 3 pages.
C. Perrin et al., "Expression of LSLCL, A New C-Type Lectin, is Closely Restricted, in Bone Marrow, to Immature Neutrophils", C. R. Acad. Sci. Paris, Sciences de la vie, vol. 324, No. 12, pp. 1125-1132, (2001).

*Primary Examiner*—Michail A Belyavskyi
(74) *Attorney, Agent, or Firm*—Finnegan, Henderson, Farabow, Garrett & Dunner, LLP

(57) ABSTRACT

The present invention relates to a method for diagnosing leukemia, pre-leukemia or aleukemic malignant blood diseases, a method of discriminating leukemia from pre-leukemia or aleukemic malignant blood diseases, a method of discriminating aplastic anemia from myelodysplastic syndrome, a method of diagnosing delayed engraftment of the hematopoietic stem cells after transplantation of the hematopoietic stem cells, and a method of diagnosing the graft versus host disease, each of said methods comprising quantifying stem cell growth factor (SCGF). The present invention also makes it possible to provide an agent for diagnosing leukemia, pre-leukemia or aleukemic malignant blood diseases and an agent for diagnosing delayed engraftment of the hematopoietic stem cells after transplantation of the hematopoietic stem cells or an agent for diagnosing graft versus host disease (GVHD), each containing as an active ingredient an antibody reacting with stem cell growth factor (SCGF).

14 Claims, 11 Drawing Sheets

(SCGF: Stem cell growth factor)

(GVHD: Graft versus host disease)
(SCGF: Stem cell growth factor)

(SCGF: Stem cell growth factor)

(SCGF: Stem cell growth factor)

(SCGF: Stem cell growth factor)

SEQUENCE LISTING

```
<160> NUMBER OF SEQ ID NOS: 11

<210> SEQ ID NO 1
<211> LENGTH: 302
<212> TYPE: PRT
<213> ORGANISM: Homo sapiens

<400> SEQUENCE: 1

Ala Arg Gly Ala Glu Arg Glu Trp Glu Gly Gly Trp Gly Gly Ala Gln
 1               5                  10                  15

Glu Glu Glu Arg Glu Arg Glu Ala Leu Met Leu Lys His Leu Gln Glu
            20                  25                  30

Ala Leu Gly Leu Pro Ala Gly Arg Gly Asp Glu Asn Pro Ala Gly Thr
        35                  40                  45

Val Glu Gly Lys Glu Asp Trp Glu Met Glu Glu Asp Gln Gly Glu Glu
    50                  55                  60

Glu Glu Glu Glu Ala Thr Pro Thr Pro Ser Ser Gly Pro Ser Pro Ser
65                  70                  75                  80

Pro Thr Pro Glu Asp Ile Val Thr Tyr Ile Leu Gly Arg Leu Ala Gly
                85                  90                  95

Leu Asp Ala Gly Leu His Gln Leu His Val Arg Leu His Ala Leu Asp
            100                 105                 110

Thr Arg Val Val Glu Leu Thr Gln Gly Leu Arg Gln Leu Arg Asn Ala
        115                 120                 125

Ala Gly Asp Thr Arg Asp Ala Val Gln Ala Leu Gln Glu Ala Gln Gly
    130                 135                 140

Arg Ala Glu Arg Glu His Gly Arg Leu Glu Gly Cys Leu Lys Gly Leu
145                 150                 155                 160

Arg Leu Gly His Lys Cys Phe Leu Leu Ser Arg Asp Phe Glu Ala Gln
                165                 170                 175

Ala Ala Ala Gln Ala Arg Cys Thr Ala Arg Gly Gly Ser Leu Ala Gln
            180                 185                 190

Pro Ala Asp Arg Gln Gln Met Glu Ala Leu Thr Arg Tyr Leu Arg Ala
```

```
                195                 200                 205
Ala Leu Ala Pro Tyr Asn Trp Pro Val Trp Leu Gly Val His Asp Arg
    210                 215                 220

Arg Ala Glu Gly Leu Tyr Leu Phe Glu Asn Gly Gln Arg Val Ser Phe
225                 230                 235                 240

Phe Ala Trp His Arg Ser Pro Arg Pro Glu Leu Gly Ala Gln Pro Ser
                245                 250                 255

Ala Ser Pro His Pro Leu Ser Pro Asp Gln Pro Asn Gly Gly Thr Leu
            260                 265                 270

Glu Asn Cys Val Ala Gln Ala Ser Asp Gly Ser Trp Trp Asp His
    275                 280                 285

Asp Cys Gln Arg Arg Leu Tyr Tyr Val Cys Glu Phe Pro Phe
290                 295                 300

<210> SEQ ID NO 2
<211> LENGTH: 224
<212> TYPE: PRT
<213> ORGANISM: Homo sapiens

<400> SEQUENCE: 2

Ala Arg Gly Ala Glu Arg Glu Trp Glu Gly Gly Trp Gly Gly Ala Gln
1               5                   10                  15

Glu Glu Glu Arg Glu Arg Glu Ala Leu Met Leu Lys His Leu Gln Glu
                20                  25                  30

Ala Leu Gly Leu Pro Ala Gly Arg Gly Asp Glu Asn Pro Ala Gly Thr
            35                  40                  45

Val Glu Gly Lys Glu Asp Trp Glu Met Glu Glu Asp Gln Gly Glu Glu
        50                  55                  60

Glu Glu Glu Glu Ala Thr Pro Thr Pro Ser Ser Gly Pro Ser Pro Ser
65                  70                  75                  80

Pro Thr Pro Glu Asp Ile Val Thr Tyr Ile Leu Gly Arg Leu Ala Gly
                85                  90                  95

Leu Asp Ala Gly Leu His Gln Leu His Val Arg Leu His Ala Leu Asp
            100                 105                 110

Thr Arg Val Val Glu Leu Thr Gln Gly Leu Arg Gln Leu Arg Asn Ala
        115                 120                 125

Ala Gly Asp Thr Arg Asp Ala Val Gln Ala Leu Gln Glu Ala Gln Gly
    130                 135                 140

Arg Ala Glu Arg Glu His Gly Arg Leu Glu Gly Cys Leu Lys Gly Leu
145                 150                 155                 160

Arg Leu Gly His Lys Cys Phe Leu Leu Ser Arg Asp Phe Glu Ala Gln
                165                 170                 175

Pro Ser Ala Ser Pro His Pro Leu Ser Pro Asp Gln Pro Asn Gly Gly
            180                 185                 190

Thr Leu Glu Asn Cys Val Ala Gln Ala Ser Asp Gly Ser Trp Trp
        195                 200                 205

Asp His Asp Cys Gln Arg Arg Leu Tyr Tyr Val Cys Glu Phe Pro Phe
    210                 215                 220

<210> SEQ ID NO 3
<211> LENGTH: 248
<212> TYPE: PRT
<213> ORGANISM: Homo sapiens

<400> SEQUENCE: 3

Glu Gly Ile Cys Arg Asn Arg Val Thr Asn Asn Val Lys Asp Val Thr
```

```
              1               5              10              15

Lys Leu Val Ala Asn Leu Pro Lys Asp Tyr Met Ile Thr Leu Lys Tyr
                20                  25                  30

Val Pro Gly Met Asp Val Leu Pro Ser His Cys Trp Ile Ser Glu Met
            35                  40                  45

Val Val Gln Leu Ser Asp Ser Leu Thr Asp Leu Leu Asp Lys Phe Ser
        50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
            180                 185                 190

Met Ala Leu Pro Ala Leu Phe Ser Leu Ile Ile Gly Phe Ala Phe Gly
        195                 200                 205

Ala Leu Tyr Trp Lys Lys Arg Gln Pro Ser Leu Thr Arg Ala Val Glu
    210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245

<210> SEQ ID NO 4
<211> LENGTH: 22
<212> TYPE: PRT
<213> ORGANISM: Homo sapiens

<400> SEQUENCE: 4

Arg Glu Trp Glu Gly Gly Gly Trp Gly Gly Ala Gln Glu Glu Glu Arg
1               5                  10                  15

Glu Arg Glu Ala Leu Cys
            20

<210> SEQ ID NO 5
<211> LENGTH: 10
<212> TYPE: PRT
<213> ORGANISM: Homo sapiens

<400> SEQUENCE: 5

Ala Arg Gly Ala Glu Arg Glu Trp Glu Gly
1               5                  10

<210> SEQ ID NO 6
<211> LENGTH: 10
<212> TYPE: PRT
<213> ORGANISM: Homo sapiens
<220> FEATURE:
<221> NAME/KEY: unsure
```

```
<222> LOCATION: (1)
<223> OTHER INFORMATION: Xaa is unsure

<400> SEQUENCE: 6

Xaa Leu Gln Glu Ala Leu Gly Leu Pro Ala
 1               5                  10

<210> SEQ ID NO 7
<211> LENGTH: 10
<212> TYPE: PRT
<213> ORGANISM: Homo sapiens

<400> SEQUENCE: 7

Asp Gln Gly Glu Glu Glu Glu Glu Glu Ala
 1               5                  10

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: oligo DNA
      base sequence

<400> SEQUENCE: 8
cccatcacca tcttccagga gc                                              22

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: oligo DNA
      base sequence

<400> SEQUENCE: 9
ttcaccacct tcttgatgtc atcata                                          26

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: DNA primer

<400> SEQUENCE: 10
gtcctctttt ccctcaaca                                                  19

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: DNA primer

<400> SEQUENCE: 11
ttttgggggc tttggtgg                                                   18
```

US 7,479,371 B2

METHOD OF JUDGING LEUKEMIA, PRE-LEUKEMIA OR ALEUKEMIC MALIGNANT BLOOD DISEASE AND DIAGNOSTIC THEREFOR

TECHNICAL FIELD

The present invention relates to a method of diagnosing leukemia, pre-leukemia or aleukemic malignant blood diseases, a method of discriminating leukemia from pre-leukemia or aleukemic malignant blood diseases, a method of discriminating aplastic anemia from myelodysplastic syndrome, a method of diagnosing the engraftment state of the hematopoietic stem cells after transplantation of the hematopoietic stem cells, or a method of diagnosing graft versus host disease (GVHD), wherein stem cell growth factor (SCGF) is quantified. The present invention also relates to an agent and a kit for diagnosing leukemia, pre-leukemia or aleukemic malignant blood diseases, for diagnosing engraftment state of the hematopoietic stem cells after transplantation of the hematopoietic stem cells, or for diagnosing graft versus host disease (GVHD), each comprising as an active ingredient an antibody reacting with stem cell growth factor (SCGF).

BACKGROUND ART

Diagnosis or post-treatment diagnosis of leukemia, pre-leukemia or aleukemic malignant blood diseases is important for determining the strategy for treating these diseases.

For diagnosing leukemia at its first occurrence, there is a method in which the white blood cell count in the peripheral blood of a patient is determined. When the white blood cell count is beyond the normal level, the occurrence of leukemia is suspected. However, the white blood cell counts also increase due to the enhancement of the immune-response within the body in the case of diseases other than leukemia, such as a cold. Hence, determination of the white blood cell counts alone may allow false-positive results. Besides, normal white blood cell counts in the peripheral blood range as broad as 4,000-8,000 cells/µL, so that false-negative cases are possibly raised. Therefore, a method for diagnosing leukemia with higher accuracy is in need.

As a method for diagnosing recurrence of leukemia, detection by RT-PCR of the WT-1 gene is mentioned [Clinical Pathology, 48, (underlining in original) 155 (2000), Blood, 84, (underlining in original) 3071 (1994), Japanese Patent No. 3122771]. This diagnostic method is complicated in handling, and requires a special device. As therapies for leukemia, pre-leukemia or aleukemic malignant blood diseases mentioned above, congenital metabolic diseases, solid cancers and the like, the hematopoietic stem cell transplantation therapy is mentioned. Drawbacks associated with the hematopoietic stem cell transplantation therapy include the HLA-type incompatibility between the hematopoietic stem cells of a donor and a patient, insufficient effect of the therapy owing to the physical condition of a patient and to infection, etc., such as non-engraftment of the transplanted hematopoietic stem cells, delayed engraftment of the hematopoietic stem cells, occurrence of graft versus host disease (hereinafter referred to as GVHD). When things turn to the worst, it may proceed to death.

Delayed engraftment of the hematopoietic stem cells can be coped with by the in-vivo administration of G-CSF to promote the engraftment of the hematopoietic stem cells. To cope with GVHD, in-vivo administration of immunosuppressants also suppresses rejection of the transplanted hematopoietic stem cells. However, there is a fear of side effects for either kind of agents, if administered in an excess amount. Therefore, it is crucial for determining the treatment strategy to diagnose or predict the engraftment of the hematopoietic stem cells or the occurrence of GVHD.

As a method of confirming the engraftment of hematopoietic stem cells after transplantation of the hematopoietic stem cells, there is a method in which white blood cell counts or platelet counts in the peripheral blood are determined. Hematopoietic stem cells can be diagnosed as being engrafted if these levels are increased. However, it sometimes requires from 10 days to a month or longer after transplantation for the hematopoietic stem cells to engraft, so that the engraftment of hematopoietic stem cells cannot be diagnosed at an early stage by only determining white blood cell counts or platelet counts in the peripheral blood.

A method for diagnosing the occurrence of GVHD includes observing skin rush or the like emerging at a recovery phase after transplantation of the hematopoietic stem cells. However, an easy and accurate method for diagnosing the occurrence of GVHD remains unknown. Moreover, any method to predict the occurrence of GVHD prior to its occurrence is unknown.

Human stem cell growth factor (hereinafter abbreviated as SCGF) is a protein comprising an amino acid sequence of SEQ. ID No. 1 or 2 [WO98/08869, Proc. Natl. Acad. Sci. USA, 94, 7577 (1997), Biochem. Biophys. Res. Comm., 249, (underlining in original) 124 (1998)].

Among antibodies known to recognize SCGF, there are polyclonal antibodies which are prepared by using SCGF obtained by genetic recombination and a partial peptide of SCGF which consists of 6-25 amino acid residues from the N-terminus, as immunogens, and monoclonal antibodies which are prepared by using SCGF purified partially from the cell culture supernatant and SCGF obtained by genetic recombination, as immunogens [WO98/08869]. The reference reports that this monoclonal antibody has a neutralizing activity, that a polyclonal antibody, which is prepared by using SCGF obtained by genetic recombination as an immunogen, reacts with SCGF obtained by genetic recombination when subjected to ELISA, and that SCGF obtained by genetic recombination can be detected by western blotting using a polyclonal antibody prepared by using a partial peptide of SCGF consisting of 6-25 amino acid residues from the N-terminus as an immunogen.

Further, there is a report as to anti-SCGF monoclonal KM2142 antibody which is prepared by using a partial peptide of SCGF consisting of 6-25 amino acid residues from the N-terminus as an immunogen [The Hematology Journal, 2, (underlining in original) 307 (2001)].

It is known that the expression levels of the SCGF gene, as revealed by northern blotting for human normal tissues, are high in the kidney, low in the heart, and nil in the brain, placenta, lung, liver, skeletal muscles and pancreas [Proc. Natl. Acad. Sci. USA, 94, (underlining in original) 7577 (1997)], high in the spleen, thymus, cecum, bone marrow, fetal liver and low in peripheral blood [Biochem. Biophys. Res. Comm., 249, (underlining in original) 124 (1998)]. Also, it is reported that, as a result of in-situ hybridization with normal new-born mice, SCGF is expressed in the bone marrow, proliferating cartilage, and in the proximal periosteum [The Hematology Journal, 2, (underlining in original) 307 (2001)].

It is further reported that while the SCGF gene expression is observed in bone marrow cell lines (HT60, KPB-M15), monocyte cell lines (THP-1, U-937), an erythroblast cell line (HEL) and a fibroblast cell line (NHF), expression of the gene is not observed in B-cell lines (U266B1, IM-9), a T-cell line (MOLT-4), an erythroblast cell line (K562), epithelial cancer cell lines (HeLaS3, A431), a melanoma cell line (Bowes), an adenovirally transformed fetal kidney cell line (293) and a fibroblast cell line (CCD-8Lu) [Proc. Natl. Acad. Sci. USA, 94, 7577 (1997)].

There has been, however, no reports with regard to differences in mRNA amounts of SCGF in the peripheral blood and in the bone-marrow blood cells from animals including humans that are either normal or suffering blood diseases, or from those that underwent transplantation of the hametopoietic stem cells.

Since the mRNA levels of tissues and cells have low correlation with the encoded proteins (correlation coefficient=0.48) [Electrophoresis, 18, 533 (1997)], it is a hard task to estimate the level of SCGF protein from that of SCGF mRNA.

Thus, the existence, function and association with diseases of SCGF protein in the body fluid such as serum and plasma and in the tissues from animals including humans are left unrevealed.

An object of the present invention is to provide a method for diagnosing leukemia, pre-leukemia or aleukemic malignant blood diseases, a method for discriminating leukemia from pre-leukemia or aleukemic malignant blood diseases, a method for discriminating aplastic anemia from myelodysplastic syndrome, and a method for diagnosing the engraftment of hematopoietic stem cells and GVHD after transplantation of the hematopoietic stem cells, and to provide an agent and a kit for diagnosing leukemia, pre-leukemia or aleukemic malignant blood diseases, and an agent and a kit for diagnosing the engraftment of hematopoietic stem cells and GVHD after transplantation of the hematopoietic stem cells.

DISCLOSURE OF THE INVENTION

The present invention relates to the following (1) to (20).
(1) A method for diagnosing leukemia, pre-leukemia or aleukemic malignant blood diseases, wherein stem cell growth factor (SCGF) in an in-vivo sample is quantified.
(2) A method for discriminating leukemia from pre-leukemia or aleukemic malignant blood diseases, wherein stem cell growth factor (SCGF) in an in-vivo sample is quantified.
(3) A method for discriminating aplastic anemia from myelodysplastic syndrome, wherein stem cell growth factor (SCGF) in an in-vivo sample is quantified.
(4) A method for diagnosing the engraftment of hematopoietic stem cells after transplantation of the hematopoietic stem cells, wherein stem cell growth factor (SCGF) in an in-vivo sample is quantified.
(5) A method for diagnosing graft versus host disease (GVHD), wherein stem cell growth factor (SCGF) in an in-vivo sample is quantified.
(6) The method according to any one of (1) to (5), wherein a method for diagnosing or discriminating is an immunological assay.
(7) The method according to (6), wherein the immunological assay is a sandwich assay.
(8) The method according to (7), wherein two kinds of antibodies reacting with different epitopes of stem cell growth factor (SCGF) are used in the sandwich assay.
(9) The method according to (8), wherein the antibodies are selected from polyclonal and monoclonal antibodies.
(10) The method according to (9), wherein the monoclonal antibodies are selected from the group consisting of a monoclonal antibody recognizing the region shown by the amino acid sequence of 6-28 amino acids, a monoclonal antibody recognizing the region shown by the amino acid sequence of 29-59 amino acids, and a monoclonal antibody recognizing the region shown by the amino acid sequence of 60-302 amino acids, all in the amino acid sequence of SEQ. ID No. 1.
(11) A diagnostic agent for leukemia, pre-leukemia or aleukemic malignant blood diseases comprising an antibody reacting with stem cell growth factor (SCGF) as an active ingredient.
(12) A diagnostic agent for the engraftment of the hematopoietic stem cells after transplantation of the hematopoietic stem cells comprising an antibody reacting with stem cell growth factor (SCGF) as an active ingredient.
(13) A diagnostic agent for graft versus host disease (GVHD) comprising an antibody reacting with stem cell growth factor (SCGF) as an active ingredient.
(14) The diagnostic agent according to any one of (11) to (13), wherein the antibody is selected from polyclonal and monoclonal antibodies.
(15) The diagnostic agent according to (14), wherein the monoclonal antibody is selected from the group consisting of a monoclonal antibody recognizing the region shown by the amino acid sequence of 6-28 amino acids, a monoclonal antibody recognizing the region shown by the amino acid sequence of 29-59 amino acids, and a monoclonal antibody recognizing the region shown by the amino acid sequence of 60-302 amino acids, all in the amino acid sequence of SEQ. ID No. 1.
(16) A diagnostic kit containing an antibody reacting with stem cell growth factor (SCGF), which is for leukemia, pre-leukemia or aleukemic malignant blood diseases, for engraftment of hematopoietic stem cells after transplantation of the hematopoietic stem cells, and for graft versus host disease (GVHD).
(17) The diagnostic kit according to (16), which contains stem cell growth factor (SCGF).
(18) A monoclonal antibody which recognizes the region shown by the amino acid sequence of 29-59 amino acids in SEQ. ID No. 1.
(19) A monoclonal antibody which recognizes the region shown by the amino acid sequence of 60-302 amino acids in SEQ ID. No. 1.
(20) A hybridoma which produces the monoclonal antibody according to (18) or (19).

1: Lane for a molecular weight marker.

2. Lane for the purified SCGF which was analyzed and silver-stained.

3. Lane subjected to western blotting using the anti-SCGF KM2142 antibody.

4. Lane subjected to western blotting using the anti-SCGF KM2804 antibody.

5. Lane subjected to western blotting using the anti-SCGF KM2945 antibody.

Figure 3:
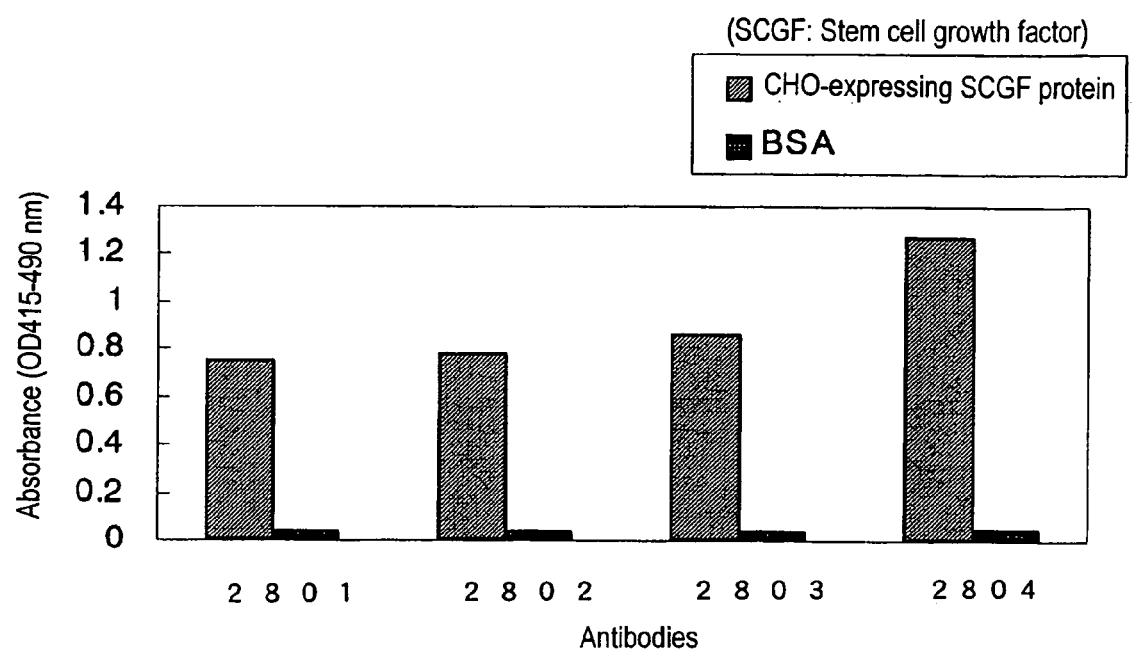

A: indicating the molecular weight of SCGF protein.
B: indicating the molecular weight of the SCGF protein Δ28 which lacks the 28th amino acid residue from the N-terminus.
C: indicating the molecular weight of the SCGF protein Δ59 which lacks the 59th amino acid residue from the N-terminus.
1: Lane for a molecular weight marker
2: Lane for the purified SCGF which was analyzed and silver-stained.
3: Lane subjected to western blotting using the anti-SCGF KM2142 antibody
4: Lane subjected to western blotting using the anti-SCGF KM2804 antibody
5: Lane subjected to western blotting using the anti-SCGF KM2945 antibody
A: indicating the molecular weight of SCGF protein
B: indicating the molecular weight of the SCGF protein Δ28 which lacks the 28th amino acid residue from the N-terminal
C: indicating the molecular weight of the SCGF protein Δ59 which lacks the 59th amino acid residue from the N-terminal FIG. 3 shows reactivity of monoclonal antibodies to the CHO cell-expressing human SCGF protein (Binding ELISA)

Figure 4:
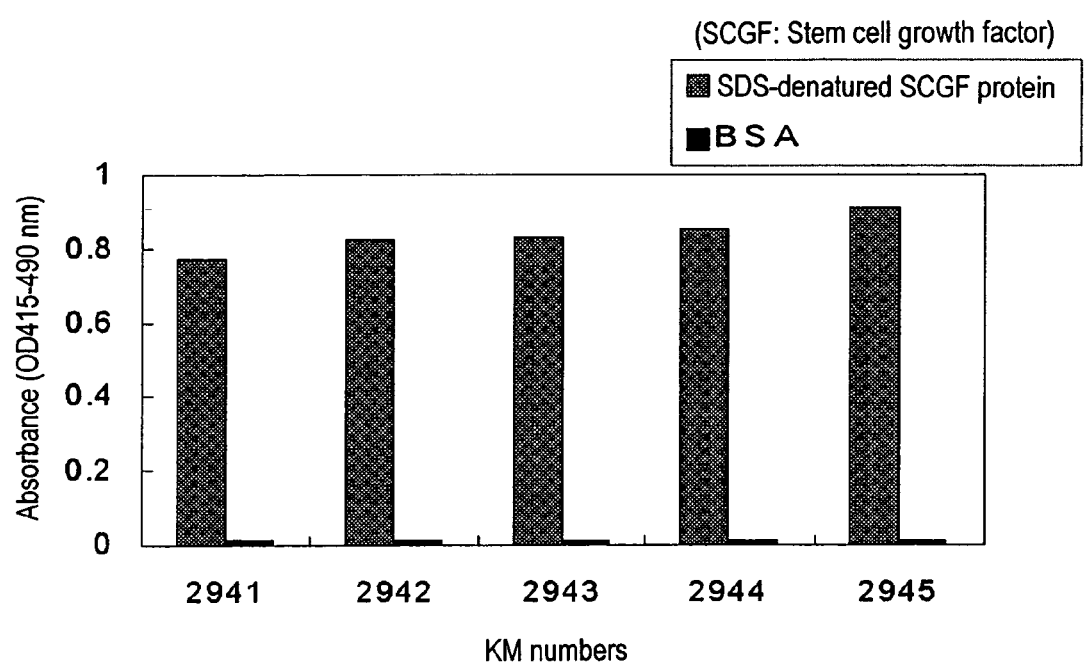

FIG. 4 shows reactivity of monoclonal antibodies to the SDS-degenerated human SCGF protein (expressing CHO cells) (Binding ELISA).

Figure 5:
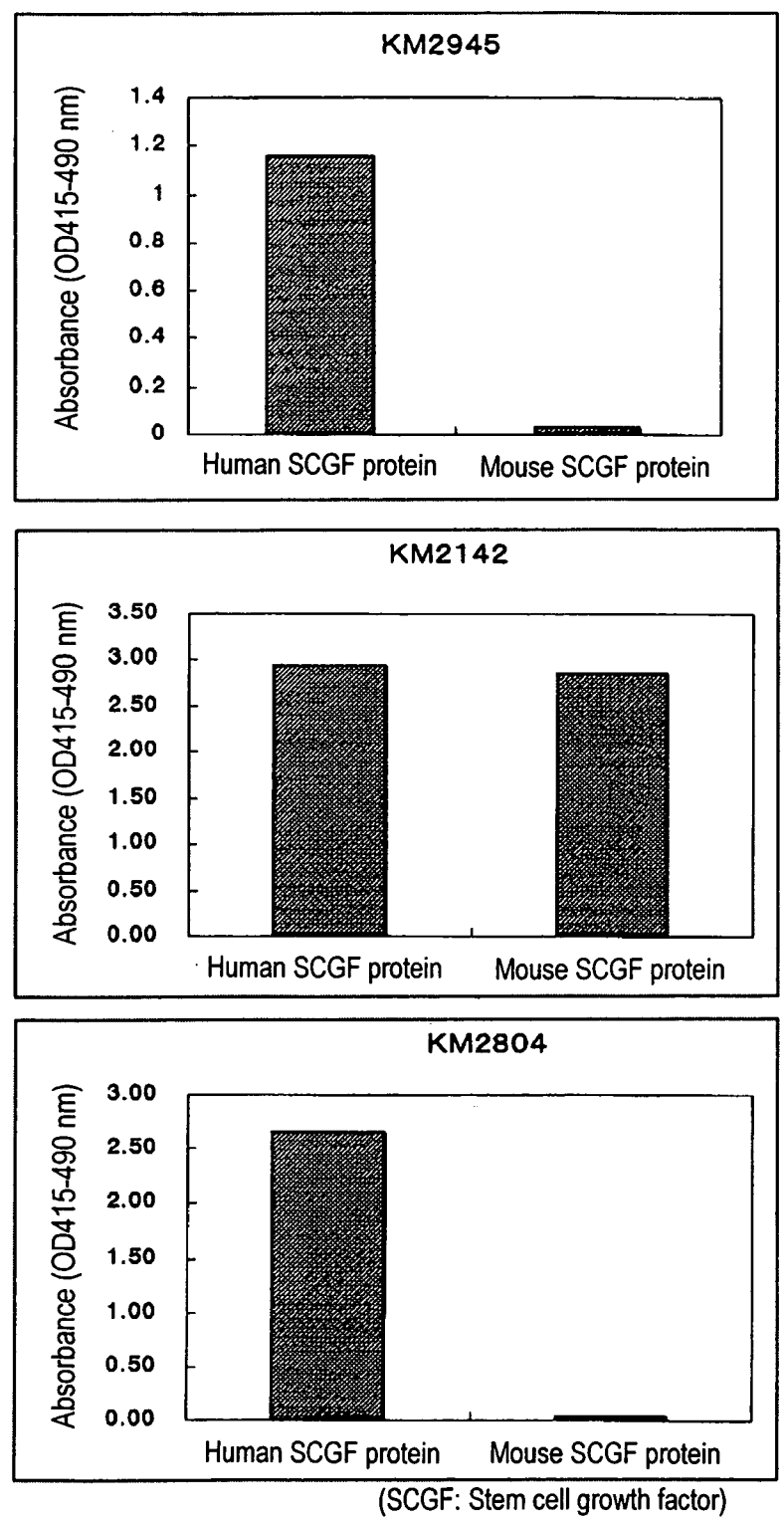

FIG. 5 shows reactivity of monoclonal antibodies to human and mouse SCGF proteins (expressing CHO cells) (Binding ELISA).

Figure 6:
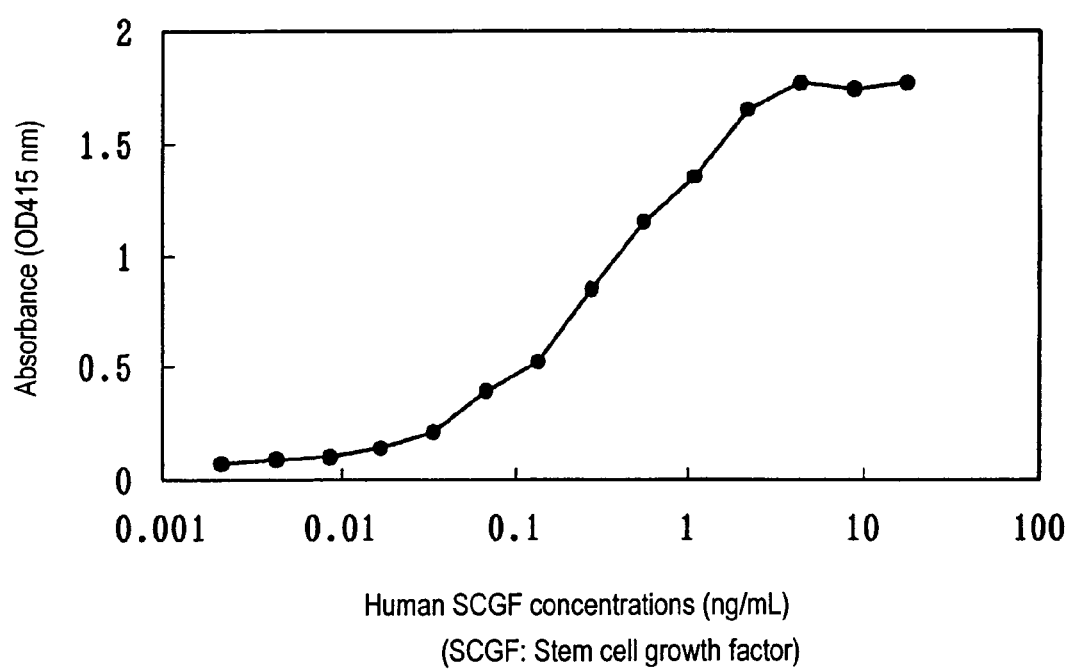

FIG. 6 shows a quantification curve for the human SCGF protein examined by sandwich ELISA using a monoclonal antibody.

Figure 7:
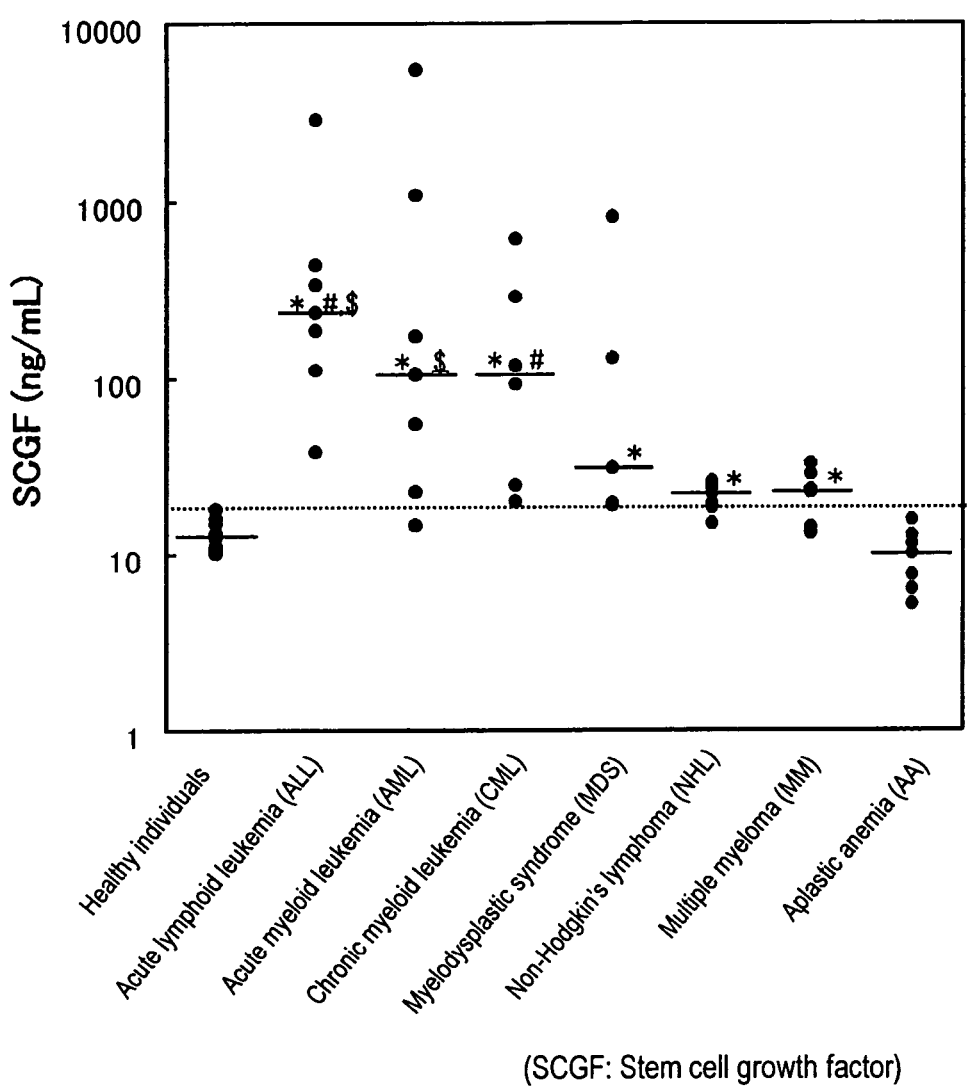
Figure 8:
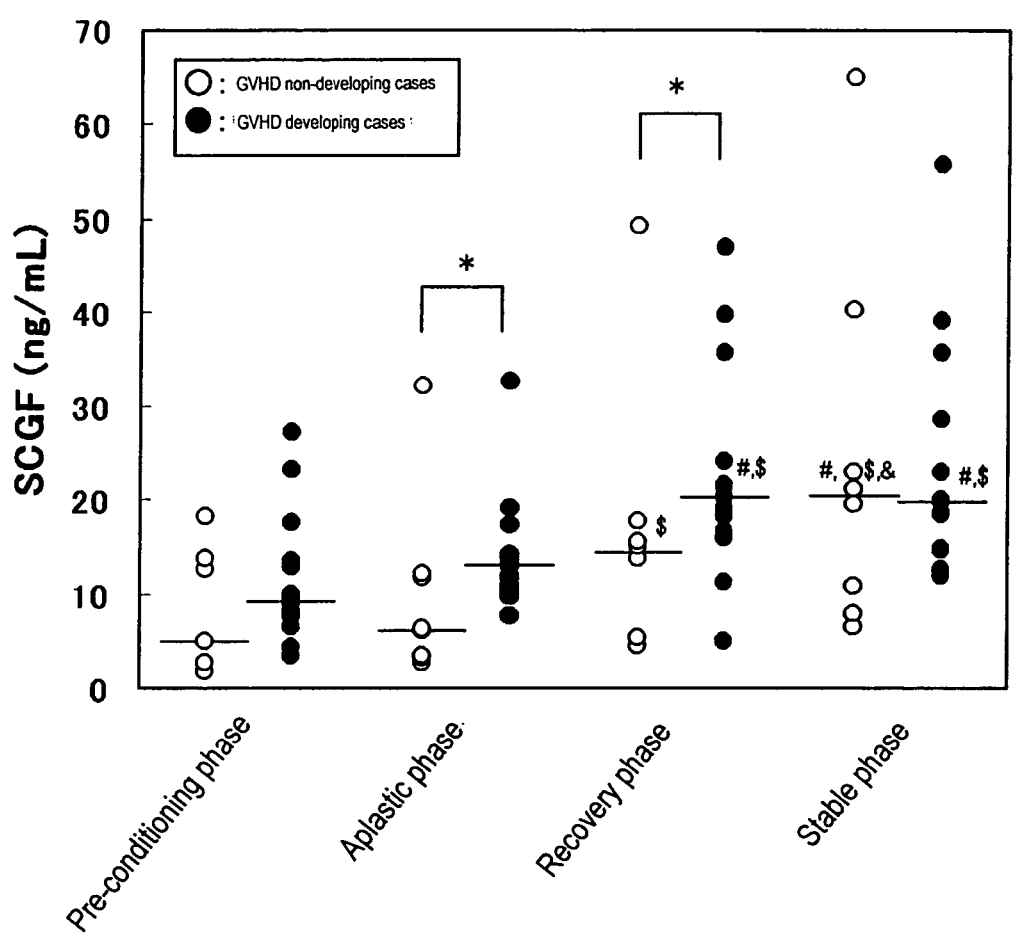
Figure 9:
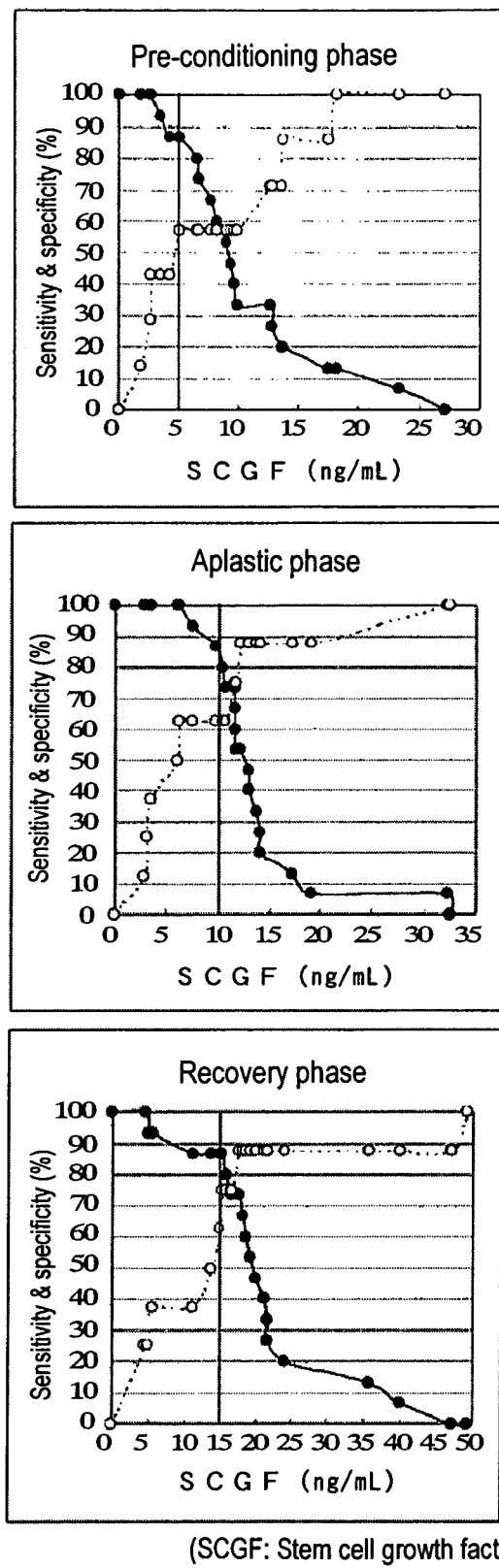

FIG. 7 shows SCGF concentrations in the sera of patients suffering various blood diseases. The horizontal full lines show the medians of various blood disease groups and the horizontal dotted line shows the cut-off value calculated from the healthy individual group (18.2 ng/mL).
*: significant difference with either normal (healthy individual group) or AA (aplastic anemia group) $p<0.05$
: significant difference with NHL (non-Hodgkin's lymphoma) $p<0.05$
$: significant difference with MM (multiple myeloma) $p<0.05$ FIG. 8 shows the difference between the cases with and without the occurrence of GVHD depending on the serum SCGF concentration in the patients who underwent transplantation of hematopoietic stem cells. The horizontal full lines show the median of each group.
*: significant difference with the cases without the occurrence of GVHD $p<0.05$
: significant difference with pre-condition phase $p<0.05$
$: significant difference with aplastic phase $p<0.05$
&: significant difference with recovery phase $p<0.05$ FIG. 9 shows relationships between detection sensitivity of the GVHD-occurred patients/specificity of the non-occurred patients and the serum SCGF concentration of the patients who underwent transplantation of the hematopoietic stem cells. ● represents sensitivity, ○ represents specificity, vertical dotted lines represent temporary cut-off values.

Figure 10:
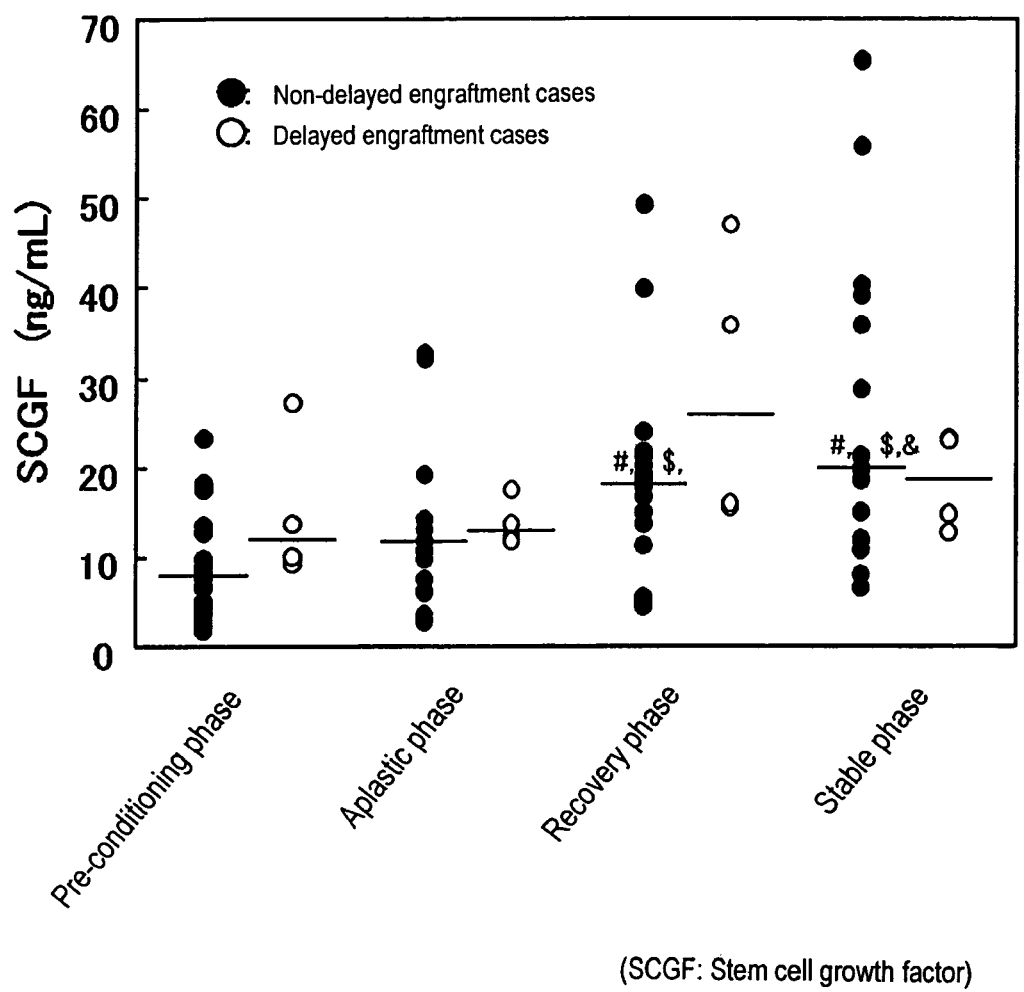
Figure 11:
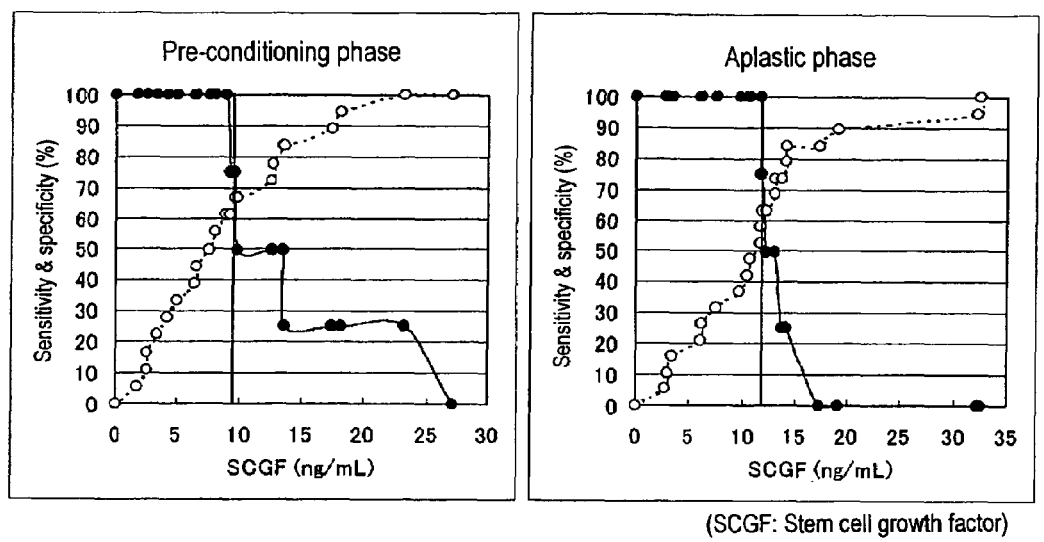

FIG. 10 shows differences between the cases for delayed and non-delayed engraftment depending on the serum SCGF concentration of the patients who underwent transplantation of the hematopoietic stem cells. The horizontal full line shows the median of each group.
: significant difference with pre-condition phase $p<0.05$,
$: significant difference with aplastic phase $p<0.05$
&: significant difference with recovery phase $p<0.05$ FIG. 11 shows relationships between the serum SCGF concentration of the patients who underwent transplantation of the hematopoietic stem cells and the detection sensitivity of the delayed engraftment/specificity of the non-delayed engraftment of hematopoietic stem cells. ● represents sensitivity, ○ represents specificity, vertical dotted lines represent temporary cut-off values.

BEST MODES FOR CARRYING OUT THE INVENTION

The present invention relates to a method for diagnosing leukemia, pre-leukemia or aleukemic malignant blood diseases.

Any type of leukemia is encompassed in the present invention as long as immature cells, such as hematopoietic cells of the hematopoietic system, have turned into tumors. Examples include acute lymphocytic leukemia (hereinafter referred to as ALL), acute myeloid leukemia (hereinafter referred to as AML), and chronic myeloid leukemia (hereinafter referred to as CML).

Any type of pre-leukemia is encompassed in the present invention as long as mature cells, such as lymphocytes of the hematopoietic system, have turned into tumors. An example includes myelodysplastic syndrome (hereinafter referred to as MDS).

Examples of aleukemic malignant blood diseases are lymphoma, myeloma and the like.

Examples of lymphoma include Hodgkin's lymphoma, non-Hodgkin's lymphoma (hereinafter referred to as NHL) and the like.

Examples of myeloma include multiple myeloma (hereinafter referred to as MM) and the like.

SCGF concentrations of in-vivo samples of patients with leukemia, pre-leukemia and aleukemic malignant blood diseases are significantly increased compared to those of healthy individuals. A cut-off value is therefore applied to the SCGF concentration in quantifying SCGF contained in the in-vivo samples collected, and it can be diagnosed as being leukemia, pre-leukemia or aleukemic malignant blood diseases when the SCGF concentration exceeds the cut-off value.

"A cut-off value" means a value set to diagnose a disease group of the interest and the non-disease group by laying focus on a substance. In diagnosing disease of the interest and the non-disease cases, diagnosis can be made for the disease of the interest as negative when the value is equal to or below the cut-off value and as positive when equal to or above the cut-off value, or likewise it can be diagnosed as positive when the value is equal to or below the cut-off value and as negative when equal to or above the cut-off value (Outline for Laboratory Tests (Rinsho kensahou teiyo), edited by Masamitsu Kanai, Kanehara & Co., Ltd.).

Sensitivity and specificity are noted as indexes used for the purpose of evaluating clinical availability of cut-off values.

A group is diagnosed with a cut-off value. Those diagnosed as positive among the disease patients are presented as "a" (true positive), those diagnosed as negative in spite of being disease patients are presented as "b" (false negative), those diagnosed as positive in spite of not being disease patients are presented as "c" (false positive), and those who are not the disease patients and diagnosed as negative are presented as "d" (true negative). According to the above diagnoses, sensitivity (a true positive rate) can be represented by a level calculated as a/(a+b) and specificity (a true negative rate) can be represented by a value calculated as d/(c+d).

In general, distribution of the measured values of a disease group of the interest partially overlaps those of the non-disease group. Therefore, sensitivity and specificity will vary by shifting a cut-off value up and down. Shifting a cut-off value downwards leads to higher sensitivity while specificity lowers. Shifting a cut-off value upwards leads to lower sensitivity while specificity mounts. Preferred is a diagnosis method in which values of both sensitivity and specificity are high. In addition, diagnosis methods in which sensitivity and specificity values do not exceed 50% are not considered as being available.

Examples of the methods for setting a cut-off value are a method in which a level at either end from the median where 95% of the non-disease group distribution is inclusive, is set as a cut-off value, and a method in which "average+doubled standard deviation (SD)" or "average−2SD" is set as a cut-off value when the non-disease group distribution exhibits a regular distribution, and so on.

In diagnosing leukemia, pre-leukemia or aleukemic malignant blood diseases, diagnosis can be given at a sensitivity of 89.5% and a specificity of 70% when a cut-off value is set at 15.0 ng/mL, and at a sensitivity of 100% and a specificity of 60% when a cut-off value is set at 13.0 ng/mL. When a cut-off value is set at 18.2 ng/mL which is "mean+2SD" from the SCGF concentration of healthy individuals, diagnosis can be given at a sensitivity of 89.5% and a specificity of 100%. Moreover, by the use of this cut-off value, leukemia can be diagnosed at a sensitivity of 95% and a specificity of 100%, aleukemic malignant blood disease at a sensitivity of 76.9% and a specificity of 100%, and pre-leukemia at a sensitivity of 100% and a specificity of 100%.

Though any in-vivo sample may be used such as blood, urine, spinal fluid or puncture fluid, blood is preferred. Examples of blood include, whole blood, plasma, serum, hemocytic laked blood, the blood cell's inner fluid and the like, among which serum or plasma are preferred.

The present invention relates to a method for discriminating leukemia from pre-leukemia or aleukemic malignant blood diseases.

SCGF concentrations of in-vivo samples of leukemia patients have been significantly increased compared to those of patients with pre-leukemia or an aleukemic malignant blood disease. Therefore, after diagnosing a sample as being leukemia, pre-leukemia or an aleukemic malignant blood disease according to a method described above, a cut-off value is further set for leukemia to be diagnosed, then it can be diagnosed as being leukemia when the SCGF concentration of the in-vivo sample collected is higher than the cut-off value and as being pre-leukemia or an aleukemic malignant blood disease when such concentration is lower than the cut-off value.

In discriminating leukemia from pre-leukemia or a leukemic malignant blood diseases, with a cut-off value set at 23.8 ng/mL, diagnosis can be given at a sensitivity of 85% and a specificity of 69.2%. Further, with a cut-off value set at 32.8 ng/mL from "average of the aleukemic malignant blood disease patients+2SD", diagnosis can be given at a sensitivity of 80% and a specificity of 100%.

The present invention relates to a method for discriminating aplastic anemia from myelodysplastic syndrome.

Aplastic anemia and myelodysplastic syndrome have pathologies characterized by abnormalities in the counts and morphology of white blood cells in the bone marrow and peripheral blood: Discrimination of the two diseases has been considered to be difficult.

The SCGF concentration of a myelodysplastic syndrome patient has been significantly increased compared to that in the blood of a healthy individual, while the blood SCGF concentration of an aplastic anemia patient is comparable to that of a healthy individual. The blood SCGF concentration of a myelodysplastic syndrome patient is significantly higher than that of an aplastic anemia patient, so that measuring the blood SCGF concentrations of patients of the two diseases enables discrimination between aplastic anemia and myelodysplastic syndrome.

For discriminating between patients of aplastic anemia and of myelodysplastic syndrome, among the patients accompanying abnormality of white blood cells, patients of the two diseases of interest can be discriminated at a sensitivity of 100% and a specificity of 100% by setting a cut-off value (average+2SD=16.6 ng/mL) from SCGF concentrations of the aplastic anemia patients and diagnosing on the basis of the cut-off value. Further, by setting the standard value between 15.6 ng/mL and 18.6 ng/mL, patients of aplastic anemia and of myelodysplastic syndrome can be discriminated at a sensitivity of 100% and a specificity of 100%.

The present invention further relates to a method for diagnosing delayed engraftment of the hematopoietic stem cells after transplantation of the hematopoietic stem cells.

Any method for transplantation of the hematopoietic stem cells can be applied as transplantation of the hematopoietic stem cells, and the examples include transplantation of bone marrows, cord blood, peripheral blood stem cells or the like.

The period from transplantation of the hematopoietic stem cells to the engraftment of hematopoietic stem cells are divided into four phases as follows based on the blood cell counts in the peripheral blood of patients. That is, pre-conditioning phase when anticancer agents are administered at a high dose prior to transplantation, aplastic phase when the blood cell counts have been decreased following transplantation, recovery phase when the blood cell counts have been recovered after transplantation, and stable phase when the hematopoietic stem cells have engrafted after transplantation.

With regard to SCGF concentrations at the pre-conditioning and aplastic phases of the in-vivo samples of the patients subjected to transplantation of the hematopoeitic stem cells, the concentrations of the in-vivo samples of the patients with delayed engraftment of the hematopoietic stem cells are higher than those of the patients without delayed engraftment of the hematopoietic stem cells. Therefore the SCGF concentration in each phase is measured. Then the SCGF concentration which is considered as possibly resulting in delayed engraftment of the hematopoietic stem cells is specified as a cut-off value. When the SCGF concentration is lower than the cut-off value, it can be diagnosed as free of delayed engraftment. When the SCGF concentration is higher than the cut-off value, it can be diagnosed that delayed engraftment should occur.

In diagnosing delayed engraftment of the hematopoietic stem cells, diagnosis can be given at a sensitivity of 75% and a specificity of 67% by affording a cut-off value of, for instance, 9.5 ng/mL for pre-conditioning phase, and at a sensitivity of 75% and a specificity of 63% by affording a cut-off value of 12 ng/mL for aplastic phase.

The present invention further relates to a method for diagnosing the occurrence of GVHD.

SCGF concentrations of in-vivo samples at aplastic and recovery phases of patients who underwent transplantation of the hematopoietic stem cells are higher in patients occurring GVHD than those in patients not occurring GVHD. Accordingly, SCGF concentration in each phase is measured, the SCGF concentration which is considered as possibly occurring GVHD is specified as a cut-off value in each phase, and it can be diagnosed GVHD is not occurred when a SCGF concentration is lower than the cut-off value and that GVHD is possibly occurring when a SCGF concentration is higher than the cut-off value.

In diagnosing occurrence of GVHD after transplantation of the hematopoietic stem cells, GVHD-occurring and non-occurring patients can be diagnosed at a sensitivity of 87% and a specificity of 57% by affording a cut-off value of, for instance, 5 ng/mL for pre-conditioning phase, and at a sensitivity of 87% and a specificity of 63% by affording a cut-off value of, for instance, 10 ng/mL for aplastic phase.

Any method such as immunological assays and molecular-biological assays can be employed as a method for measuring stem cell growth factor (hereinafter referred to as SCGF) in in-vivo samples, and immunological assays are preferred.

Any method is encompassed by such immunological assays as long as it is a method using antigen-antibody reaction such as immunoassays, immunoblotting methods, agglutination test, complement fixation test, hemolysis test, precipitation test, colloidal gold method, chromatography methods or immunostaining methods, and immunoassays are preferred.

Examples of molecular-biological assays include the RT-PCR method, northern blotting method, in situ hybridization method and the like.

An immunoassay is a method to detect or to quantify antibodies or antigens by using antigens or antibodies that are labeled in various ways, and the examples are given on the basis of labeling means for antigens or antibodies, which include radioimmuno assay (RIA), enzyme-linked immunosorbent assay (EIA or ELISA), fluorescent immunoassay (FIA), luminescent immunoassay, physicochemical assays (TIA, LAPIA, PCIA), flow cytometry, among which enzyme-linked immunosorbent assay is preferred.

Any known (Enzyme-linked Immunosorbent Assay, edited by Eiji Ishikawa et al., Igaku-Shoin Ltd.) radioisotope may be used as a radioactive label in radioimmunoassay. For instance, $^{32}P$, $^{125}I$, $^{131}I$ and the like may be used.

Any known (Enzyme-linked Immunosorbent Assay, edited by Eiji Ishikawa et al., Igaku-Shoin Ltd.) enzyme may be used as an enzyme label in an enzyme-linked immunosorbent assay. For instance, alkaline phosphatase, peroxidase, luciferase and the like may be used.

In the enzyme-linked immunosorbent assay, measurement/detection is carried out by measuring substances produced through enzymatic action, and various measuring methods can be employed including a method for measuring absorbance of a substance having absorption maximum at the ultraviolet range or visible range, a method for measuring fluorescence intensity of the fluorescent material produced, a method for measuring luminescence intensity of the substance produced. For instance, when alkaline phosphatase is used as an enzyme label, e.g. 4-nitrophenyl phosphate and the like are given as a substrate for alkaline phosphatase which produces, through the action of alkaline phosphatase, a substance having absorption maximum at the ultraviolet range or visible range. 4-nitrophenyl phosphate is converted to 4-nitrophenol by alkaline phosphatase. As a substrate for alkaline phosphatase which give rise to luminescence through the action of alkaline phosphatase, the followings are exemplified; 3-(2'-spiroadamantane)-4-methoxy-4-(3'-phosphoryloxine)phenyl-1,2-dioxetane disodium salt (AMPPD), 2-chloro-5-{4-methoxyspiro[1,2-dioxetane-3,2'-(5'chloro) tricyclo[3.3.1$^{3,7}$]decane]-4-yl}phenylphosphate disodium salt (CDP-Star™), 3-{4-methoxyspiro[1,2-dioxetane-3,2'-(5'-chrolo)tricyclo[3.3.1$^{3,7}$]decane]-4-yl}phenylphosphate disodium (CSPD™), [10-methyl-9(10H)-acridinyl iden]phenoxymethyl phosphate disodium salt (Lumigen™ APS-5), etc. Also, as a reagent which forms dye through the action of alkaline phosphatase, AmpliQ (DAKO Corp.), an enzyme cycling reaction reagent containing NADPH, a substrate of alkaline phosphatase, is exemplified.

As a luminescent label used in the luminescent immunodetection methods, any known [Biological luminescence and Chemiluminescence, edited by Kazuhiro Imai, Hirokawa Shoten; Clinical Tests 42 (1998)] luminescent material may be used. For example, acridinium ester, rofin and the like may be used.

As a fluorescent label used in the fluorescent immunodetection methods, any known [Fluorescence-Antibody method, Akira Kawaoi, Soft Science, Inc.] fluorescence may be used. For example, FITC, RITC and the like may be used.

As an assay in immunoassays, competitive method and sandwich method [Immunology illustrated, 5$^{th}$ Edition (Nankodo)] are exemplified, and sandwich method is preferred.

The procedure of a sandwich assay is described as follows. A second antibody (secondary antibody) is simultaneously or independently reacted with the object substance in a sample together with the primary antibody that was bound through the antigen-antibody reaction. Then the object substance in the sample is detected or quantified with the use of the same or different antibodies. In many cases, this method comprises in the course of a measuring operation, a step to wash away unreacted sample components or components of the measuring system in the sample. For example, after the first antibody (primary antibody) is fixed to the solid phase, a sample to be measured is brought into contact with the first antibody. Unreacted sample components in the sample are washed and removed from the reaction system. Then the second antibody (secondary antibody) is reacted with the complex of the object substance in the sample and the first antibody that were bound through the antigen-antibody reaction. After components, such as a secondary antibody, that were not involved in the reaction that occurred within the measuring system are washed and removed, the object substance in the sample in the reaction system is detected or quantified.

Examples of solid phases used in the sandwich assay include, a polyvinylchloride microtiter plate, a polystyrene microtiter plate and the like.

Either of polyclonal antibodies and monoclonal antibodies may be used as antibodies for sandwich assay, and antibody fragments such as Fab, Fab', $F(ab)_2$ may be used as well.

As for combinations of primary and secondary antibodies for use in sandwich assay, any combination of antibodies may be accepted as long as the antibodies for combination recognize different epitopes, yet it is preferred that at least one of the antibodies is a monoclonal antibody.

Examples of monoclonal antibodies for use in the sandwich assay of the present invention include a monoclonal antibody which recognizes the region shown by the amino acid sequence of 6-28 amino acids in SEQ. ID No. 1, a monoclonal antibody which recognizes the region shown by the amino acid sequence of 29-59 amino acids in SEQ. ID No. 1, and a monoclonal antibody which recognizes the region shown by the amino acid sequence of 60-302 amino acids in SEQ. ID No. 1.

As a monoclonal antibody recognizing the region shown by the amino acid sequence of 6-28 amino acids in SEQ. ID No. 1, monoclonal KM2142 antibody produced by KM2142 hybridoma [The Hematology Journal, 2, 307 (2001)] is mentioned. As a monoclonal antibody recognizing the region shown by the amino acid sequence of 29-59 amino acids in SEQ. ID No. 1, monoclonal KM2804 antibody produced by KM2804 hybridoma is mentioned. As a monoclonal antibody recognizing the region shown by the amino acid sequence of 60-302 amino acids in SEQ. ID No. 1, monoclonal KM2945 antibody produced by KM2945 hybridoma is mentioned.

KM2142 hybridoma producing monoclonal KM2142 antibody, KM2804 hybridoma producing monoclonal KM2804 antibody and KM2945 hybridoma producing monoclonal KM2945 antibody were deposited at International Patent Organism Depositary, National Institute of Advanced Industrial Science and Technology (Central 6, 1-1 Higashi, Tsukuba, Ibaraki) on Feb. 26, 2002 as FERM BP-7922, FERM BP-7923 and FERM BP-7924, respectively.

The monoclonal antibodies mentioned above recognize SCGF at different sites so that these can be used in combination for sandwich assay. A preferable combination of antibodies is the combination of a monoclonal antibody recognizing the region shown by the amino acid sequence of 6-28 amino acids in SEQ. ID No. 1, i.e. monoclonal KM2142 antibody produced by KM2142 hybridoma [The Hematology Journal, 2, 307 (2001)] and a monoclonal antibody recognizing the region shown by the amino acid sequence of 29-59 amino acids in SEQ. ID No. 1, i.e. monoclonal KM2804 antibody produced by KM2804 hybridoma (FERM BP-7923).

A specific example of a method for detecting or quantifying SCGF by the sandwich assay of the present invention is described below.

First, an anti-SCGF antibody (primary antibody) mentioned above is absorbed and immobilized on the surface of an appropriate carrier for immobilization. For instance, a primary antibody is diluted with an appropriate buffer, e.g. phosphate buffer, borate buffer, carbonate buffer and the like, then brought into contact with the solid carrier surface and allowed to react for 30 min or longer at 4-37° C., and thus the primary antibody can be immobilized.

Next, protein-binding ability of the immobilized carrier surface is blocked. For instance, any free binding group on the immobilized carrier surface is brought into contact with a blocking buffer.

Examples of blocking buffer include a buffer containing 1-10% bovine serum albumin or 10-30% Block Ace (Snow Brand Milk Products Co. Ltd.), e.g. phosphate buffer, borate buffer, carbonate buffer and the like.

Blocking treatment may be carried out by raising reaction for 30 min or longer at 4-37° C.

Next, the primary antibody is brought into contact with in-vivo samples. In-vivo samples may be diluted as necessary with a buffer e.g. phosphate buffer, borate buffer, carbonate buffer, etc. containing for example 0.01-1% bovine serum albumin.

The primary antibody and in-vivo samples can be brought into contact by raising reaction for 30 min or longer at 4-37° C.

After the contact, the samples are washed several times as necessary with a buffer e.g. phosphate buffer, borate buffer, carbonate buffer, etc. containing a surfactant such as Tween 20.

In the course of this process, SCGF in in-vivo samples will be immobilized to the immobilized carrier via anti-SCGF antibody due to its specific binding with the anti-SCGF antibody that has been immobilized in advance.

The aforementioned carrier to which SCGF is immobilized is then brought into contact with a solution containing a secondary antibody.

As a secondary antibody, any anti-SCGF antibody having a different epitope from that of the primary antibody may be used. Also, a secondary antibody may be labeled in advance as necessary with any of the labels mentioned above.

For removing unabsorbed secondary antibody, the carrier is washed several times with a buffer e.g. phosphate buffer, borate buffer, carbonate buffer and the like containing as necessary a surfactant such as Tween 20. This process leads the secondary antibody to bind to the immobilized carrier via the primary antibody and SCGF having been bound to the carrier in advance, and the amount of the secondary antibody bound will reflect the SCGF amount in in-vivo samples.

The secondary antibody thus immobilized can be determined on the basis of labels of the secondary antibody. Besides, a third antibody specific to the secondary antibody may be used, which is labeled in various ways to detect or determine labeling for the third antibody.

As described above, the amount of the bound secondary antibody is determined, a calibration curve is constructed using a standard substance, and the SCGF amount in in-vivo samples can be determined.

A calibration curve can be obtained by providing as a standard substance a solution serially diluted several fold which contains a human SCGF protein with a known concentration, and by carrying out the sandwich assay described above using in-vivo samples.

For an antibody to SCGF contained in a diagnostic agent for leukemia, pre-leukemia or aleukemic malignant blood diseases, a diagnostic agent for delayed engraftment of the hematopoietic stem cells after transplantation of the hematopoietic stem cells, and a diagnostic agent for GVHD occurrence, of the present invention, any antibody reacting with SCGF such as polyclonal antibodies, monoclonal antibodies or antibody fragments may be used, and monoclonal antibodies are preferred.

Examples of monoclonal antibodies are a monoclonal antibody which recognizes the region shown by the amino acid sequence of 6-28 amino acids in SEQ. ID No. 1, a monoclonal antibody which recognizes the region shown by the amino acid sequence of 29-59 amino acids in SEQ. ID No. 1, and a monoclonal antibody which recognizes the region shown by the amino acid sequence of 60-302 amino acids in SEQ. ID No. 1.

As a monoclonal antibody recognizing the region shown by the amino acid sequence of 6-28 amino acids in SEQ. ID No. 1, monoclonal KM2142 antibody produced by KM2142 hybridoma (FERM BP-7922) is mentioned. As a monoclonal antibody recognizing the region shown by the amino acid sequence of 29-59 amino acids in SEQ. ID No. 1, monoclonal KM2804 antibody produced by KM2804 hybridoma (FERM BP-7923) is mentioned. As a monoclonal antibody recognizing the region shown by the amino acid sequence of 60-302 amino acids in SEQ. ID No. 1, monoclonal KM2945 antibody produced by KM2945 hybridoma (FERM BP-7924) is mentioned.

A kit of the present invention consists of a combination of devices or reagents, however, a kit with different constitution or conformation will be encompassed by the kit of the present invention in so far as the kit contains a substance that is essentially the same as each component described below or essentially the same as part of the component.

Reagents contain antibody reacting with SCGF and further contain, where appropriate, dilution for in-vivo samples, solid phase for immmobilizing antibodies, reaction buffer, washing solution, a labeled secondary antibody or an antibody fragment thereof, detection reagent for a label, standard substance such as SCGF.

Examples of dilutions for in-vivo samples are aqueous solutions containing proteins such as BSA or casein in addition to surfactants or buffer.

For preparing a solid phase for immobilizing antibody, various high-polymer materials are formed into a shape to meet the use, on which an antibody or the antibody fragment of the present invention is applied to give a solid phase. The solid phase for immobilizing antibodies are in the form of tubes, beads, plates, microparticles such as latex, sticks, etc. Examples of materials are high-polymer materials such as polystyrene, polycarbonate, polyvinyltoluene, polypropylene, polyethylene, polyvinyl chloride, nylon, polymethacrylate, gelatin, agarose, cellulose and polyethylene terephthalate, glass, ceramics, metals, and the like. Antibodies can be immobilized on solid phase by the known physical and chemical methods or by the combination of these methods. For instance, antibodies and the like are hydrophobically immobilized on a polystylene 96-well microtiter plate for immunoassays.

Any reaction buffer may be used which provides a solvent environment at the binding reaction of an antibody in the solid phase for immobilizing antibodies and an antigen in the in-vivo samples: The examples include surfactants, buffers, proteins such as BSA and casein, antiseptics, stabilizers and reaction promoters.

As for washing solutions, a solution is exemplified which contains buffer agents such as phosphate, Tris (tris-hydroxy-methyl-amino-methane) or Good's buffers such as HEPES and MOPS, and further contains at least one kind selected from the group consisting of surfactants such as Tween20, Tween40, Tween60, Tween80 and Triton™ X-705; salts such as NaCl, KCl and ammonium sulphate; proteins such as BSA and casein; antiseptics such as sodium azide; denaturants such as guanidine hydrochloride, urea, sodium dodecyl sulphate; and stabilizers such as polyethylene glycol, carboxymethylcellulose, dextran sulphate and chondroitin sulphate. Specific examples are Tween/PBS consisting of 0.15 mol/L sodium chloride, 0.05% Tween 20 and 10 mmol/L phosphated buffer (pH 7.4), Tween/TBS consisting of 0.15 mol/L sodium chloride, 0.05% Tween20 and 10 mmol/L Tris-HCl buffer (pH 7.4) and the like.

As the labeled secondary antibodies and antibody fragments thereof, antibodies or antibody fragments thereof of the present invention labeled with labeling enzymes such as horseradish peroxidase (HRP), bovine intestine alkaline phosphatase, β-galactosidase, and those admixed with buffers, proteins such as BSA and casein, antiseptics, etc. are used.

The detection reagents for the labels vary depending on the aforementioned labeling enzymes. For horseradish peroxidase, substrates for measuring absorbance such as tetramethylbenzidine and ortophenylenediamine, fluorescent substrates such as hydroxyphenyl propionic acid and hydroxyphenyl acetic acid, and luminescent substrates such as luminor are exemplified. For alkaline phosphatase, substrates for measuring absorbance such as 4-nitrophenylphosphate, and fluorescent substrates such as 4-methylumbelliferylphosphate are exemplified.

Standard substances include SCGF prepared by the method described in WO98/08869, and a peptide containing epitopes for two kinds of antibodies used in a kit.

The present invention relates to a monoclonal antibody recognizing a region shown by the amino acid sequence of 29-59 amino acids in SEQ. ID No. 1, and a monoclonal antibody recognizing a region shown by the amino acid sequence of 60-302 amino acids in SEQ. ID No. 1.

Monoclonal KM2804 antibody produced by KM2804 hybridoma (FERM BP-7923) is mentioned as a monoclonal antibody recognizing a region shown by the amino acid sequence of 29-59 amino acids in SEQ. ID No. 1. Monoclonal KM2945 antibody produced by KM2945 hybridoma (FERM BP-7924) is mentioned as a monoclonal antibody recognizing a region shown by the amino acid sequence of 60-302 amino acids in SEQ. ID No. 1.

Monoclonal antibodies for use in the present invention can be produced by a known method for producing monoclonal antibodies.

A method for producing a monoclonal antibody for use in the present invention will be described below in detail.

(1) Preparation of Antigens

Examples of antigens are a human SCGF protein obtained by introducing an expression vector, which contains cDNA encoding human SCGF, into *E. coli*, yeast, insect cells, animal cells, etc., and a synthetic peptide having a partial sequence of human SCGF obtained by peptide synthesis.

As a partial antigenic peptide, a partial sequence of a protein in a stretch of approximately 5-30 residues is selected. In order to obtain an antibody recognizing the protein having a native conformation without any denaturation, a partial sequence present on the protein surface in a three-dimensional structure needs to be selected as an antigenic peptide. A portion present on the protein surface in a three-dimensional structure can be speculated by predicting a partial sequence with high hydrophilicity according to a method of Kyte and Doolittle [Journal of Molecular Biology, 157, 105-132 (1982)] and the like. This is because, in general, low hydrophilic portions are often present inside a protein in a three-dimensional structure, and high hydrophilic portions are often present on the protein surface. In addition, N- and C-terminals of a protein are often present on the protein surface. Information about the protein secondary structure can also be referred to. Portions with a turn structure or random-coil structure can be considered to be suitable as an antigenic peptide in the protein secondary structure predicted on the basis of an amino acid sequence according to the method of Chou-Fasman [Advances in Enzymology, 47, 45-147 (1978)] and the like. However, a partial peptide thus selected is not always the antigen that establishes the antibody of the interest.

Cysteine is added to a partial peptide on its terminus for the cross-linking with the protein. When an internal sequence of the protein is selected, the N-terminus of the peptide is acetylated and the C-terminus is amidated, if necessary.

Partial peptides can be synthesized by common methods such as liquid-phase peptide synthesis method and solid-phase peptide synthesis method, methods combining these methods, or methods similar to these [International Journal of Peptide Protein Research, 35, 161-214 (1990); Solid-Phase Peptide Synthesis, Methods in Enzymology, vol. 289, edited by Gregg B. Fields, Academic Press (1997); Peptide Synthesis Protocols, Methods in Molecular Biology, vol. 35, edited by Michael W. Pennington & Ben M. Dunn, Humana Press (1994)].

Automatic peptide synthesizers may also be used. Peptide synthesis on a peptide synthesizer can be carried out on a commercial peptide synthesizer such as a peptide synthesizer manufactured by Shimadzu Corp., a peptide synthesizer manufactured by Advanced ChemTech Inc., USA (hereinafter referred to as ACT) according to their synthesis program by using Nα-Fmoc- or Nα-Boc-amino acids and the like whose side-chains are suitably protected. Protected amino acids and carrier resins as raw materials are available from ABI, Shimadzu Corp., Kokusan Chemical Co., Ltd., Nova-Biochem Corp., Watanabe Chemical Ind. Ltd., ACT, AnaSpec Inc., Peptide Institute, Inc., and so on.

(2) Immunization of Animals and Preparation of Antibody-producing Cells

Mice, rats or hamsters of 3 to 20 weeks of age are immunized with antigens prepared in (1), and the antibody-producing cells in the spleen, lymph nodes and peripheral blood of the animals are collected.

The animals are immunized with antigens subcutaneously, intravenously or intraperitoneally together with suitable adjuvants [e.g. complete freund's adjuvant, or alminium hydroxide gel and pertussis vaccine]. When an antigen is a partial peptide, the antigen is conjugated with a carrier protein such as BSA (bovine serum albumin) or KLH (Keyhole Limpet Hemocyanin), and the conjugate is then used as an immunogen.

Antigen is administered 3-10 times at 1-2 week-intervals after the first administration. Blood is collected from the venous plexus in ocular fundus 3 to 7 days after each administration. The collected blood is examined whether the sera react with the antigen or not by an enzyme-linked immunosorbent assay [Antibodies—A Laboratory Manual, Cold Spring Harbor Laboratory, 1988], etc. Mice, rats or hamsters whose sera exhibited sufficient antibody titers against the immunized antigen are provided as source for antibody-producing cells.

Three to seven days after the final administration of antigenic substance, the spleens are excised from the immunized mice, rats or hamsters, and splenocytes for fusion of antibody-producing cells and myeloma cells are collected therefrom. The spleens are chopped in a MEM medium (Nissui Pharmaceutical Co., Ltd.), loosened with a forcep and subjected to centrifugation (1,200 rpm, 5 min). The supernatants are then discarded, and the spleens are treated with a Tris-ammonium chloride buffer (pH 7.65) for 1-2 min to remove erythrocytes and washed three times in a MEM medium, which are then provided as splenocytes for fusion.

(3) Preparation of Myeloma Cells

Cell lines obtained from mice are used as myeloma cells. For instance, the myeloma cell lines from the 8-azaguanine-resistance mice (BALB/c-derived) such as P3-X63Ag8-U1 (P3-U1) [Current Topics in Microbiology and Immunology, 18: 1-7 (1978)], P3-NS1/1-Ag41 (NS-1) [European J. Immunology, 6: 511-519 (1976)], SP2/O-Ag14 (SP-2) [Nature, 276: 269-270 (1978)], P3-X63-Ag8653 (653) [J. Immunology, 123: 1548-1550 (1979)], and P3-X63-Ag8 (X63) [Nature, 256: 495-497 (1975)] are used. These cell lines are subcultured in a 8-azaguanine medium [a RPMI-1640 medium supplemented with glutamine (1.5 mmol/L), 2-mercaptoethanol ($5\times10^{-5}$ mol/L), Gentamycin (10 μg/mL) and fetal calf serum (FCS) (hereinafter referred to as a normal medium), to which 8-azaguanine (15 μg/mL) is further added thereto], but they are subcultured in a normal medium 3 to 4 days prior to the cell fusion so that $2\times10^7$ or more cells will be reserved on the day of fusion.

(4) Cell Fusion

Antibody-producing cells immunized in (2) and myeloma cells obtained in (3) are well washed in MEM medium or PBS (1.83 g disodium phosphate, 0.21 g monopotassium phosphate, 7.65 g salt, 1 L distilled water, pH 7.2), and the antibody-producing cells and myeloma cells are mixed in the ratio of 5-10:1. After the cell mixture is centrifuged (1,200 rpm, 5 min), the supernatant is discarded and the precipitated cells are well loosened, to which a mixed solution of 2 g of polyethylene glycol-1,000 (PEG-1,000), 2 mL MEM and 0.7 mL dimethyl sulfoxide is added at 0.2-1 mL per $10^8$ antibody-producing cells under stirring at 37° C. To this mixture, 1-2 mL of MEM medium is added every 1-2 min for several times, and MEM medium is further added thereto to give the total volume of 50 mL, which was subjected to centrifugation (900 rpm, 5 min). The supernatant is discarded, and the cells are gently loosened. The cells are then drawn in a measuring pipette and blown out into a 100 mL of HAT medium [a normal medium supplemented with hypoxanthine ($10^{-4}$ mol/L), thymidine ($1.5\times10^{-5}$ mol/L) and aminopterin ($4\times10^{-7}$ mol/L)] to allow gentle suspension of the cells. The suspension is pipetted into a 96-well culture plate at 100 μL/well and cultured in a 5% $CO_2$ incubator for 7 to 14 days at 37° C.

A part of the culture supernatant is collected after the cultivation and subjected to, for example, an enzyme-linked immunosorbent assay as described below, to select cells which react to human SCGF but do not react to antigens free from human SCGF. Subsequently, cloning is repeated twice using a limiting dilution method [a HT medium (HAT medium removed of aminopterin) is used for the first time and a normal medium is used for the second time], and those observed for stable and high antibody titers are selected as the human SCGF monoclonal antibody-producing hybridoma lines.

Enzyme-linked Immunosorbent Assay

Antigens or antigen-expressing cells, etc. are coated onto a 96-well plate, and the culture supernatant of the hybridoma or purified antibody obtained by the method described above are allowed to react as a primary antibody.

After the reaction with a primary antibody, the plate is washed, and a secondary antibody is added thereto.

A secondary antibody is an antibody which can recognize the immunoglobulin of the primary antibody and which is labeled with biotin, enzymes, chemiluminescent substances or radioactive compounds, etc. Specifically, when a mouse is used for preparing a hybridoma, an antibody capable of recognizing the mouse immunoglobulin is used as a second antibody.

After the reaction, a reaction is raised depending on the substance used for labeling the second antibody, then a hybridoma which produces a monoclonal antibody reacting specifically to the antigen is selected.

(5) Preparation of Monoclonal Antibodies

The anti-human SCGF monoclonal antibody-producing hybridoma cells obtained in (4) are intraperitoneally injected to the 8-10 week-old mice or nude mice that have been Pristane-treated [breeding for 2 weeks after intraperitoneal injection of 0.5 mL of 2, 6, 10, 14-tetramethylpentadecane (Pristane)] at $2\times10^6$-$5\times10^7$ cells/mouse. The hybridomas turned into ascites tumor 10 to 21 days after the injection. Ascitic fluid is collected from the mice, and the solid is removed by centrifugation (3,000 rpm, 5 min), which is subjected to salting out with 40-50% ammonium sulfate. Then, the ascitic fluid is purified either by caprylic acid precipitation or with DEAE-sepharose column, protein-A column or gel filtration column to collect IgG or IgM fractions to give purified monoclonal antibodies.

Subclasses of the antibodies are determined by an enzyme-linked immunosorbent assay using a subclass typing kit. Proteins are quantified by Lawry method and from the absorbance at 280 nm.

EXAMPLES

Example 1

Production of the Anti-human SCGF Monoclonal Antibody by Using a Partial Peptide of Human SCGF (1) Synthesis of a Partial Peptide of Human SCGF The sequence of human SCGF protein is analyzed, and Compound 1 (SCGF-1) was selected as a partial sequence which is presumably suitable as an antigen from among high-hydrophilic portions, N-terminal, C-terminal, portions with a turn structure and random-coil structure in the secondary structure.

(Brevity Codes)

The brevity codes for amino acids and their protecting groups used in the present invention comply with the recommendation of IUPAC-IUB Joint Commission on Biochemical Nomenclature concerning biochemical nomenclatures [European Journal of Biochemistry, vol. 138, p. 9 (1984)].

The following brevity codes represent the corresponding amino acids as listed below unless otherwise stated.
- Ala: L-Alanine
- Arg: L-Arginine
- Cys: L-Cysteine
- Gln: L-Glutamine
- Glu: L-Glutamic acid
- Glx: L-Glutamic acid
- Gly: Glycine
- Leu: L-Leucine
- Trp: L-Tryptophan The following brevity codes represent the corresponding protecting groups of the amino acids and the side-chain protecting amino acids as listed below.
- Fmoc: 9-fluorenil methyloxycarbonyl
- tBu: t-butyl
- Trt: trithyl
- Boc: t-butyloxycarbonyl
- Pmc: 2,2,5,7,8-pentamethylchroman-6-sulphonyl
- Fmoc-Arg (Pmc)-OH: Nα-9-fluorenil methyloxycarbonyl-N$^g$-2,2,5,7,8-pentamethylchroman-6-sulphon yl-L-arginine
- Fmoc-Gln (Trt)-OH: Nα-9-fluorenil methyloxycarbonyl-Nε-trithyl-L-glutamine
- Fmoc-Glu (OtBu)-OH: Nα-9-fluorenil methyloxycarbonyl-L-glutamic acid-γ-t-butylester
- Fmoc-Trp (Boc)-OH: Nα-9-fluorenil methyloxycarbonyl-N$^{ind}$-t-butyloxycarbonyl-L-tryptophan The following brevity codes represent the corresponding reaction solvents, reaction reagents, etc. as listed below.
- PyBOP: benzotriazole-1-yloxy tripyrrolidino phosphonium hexafluoro phosphate
- HOBt: N-hydroxybenzotriazol
- NMM: N-methylmorpholine
- DMF: N,N-dimethylformamide
- TFA: trifluoro acetate Physicochemical properties of the compound was determined by the following methods in the following Examples.

Mass spectroscopy was carried out by either FAB-MS method using JMS-HX110A from JEOL Ltd. or MALDI-TOFMS method using REFLEX, a mass spectrometer from Bruker. Amino acid analysis was carried out by the method of Cohen, S. A. et al [Analytical Biochemistry, 222, 19 (1994)]. Hydrolysis was carried out for 20 h at 110° C. under a hydrochloric steam, and the amino acid composition of the hydrolytic substance was analyzed by using a Waters AccQ-Tag amino acid analyzer (Waters Corp.).

[1] Synthesis of Compound 1 (SCGF-1) (SEQ. ID NO: 4) (Ac-Arg-Glu-Trp-Glu-Gly-Gly-Trp-Gly-Gly-Ala-Gln-Glu-Glu-Glu-Arg-Glu-Arg-Glu-Ala-Leu-Cys-OH)

Thirty mg of carrier resin (H-Cys (Trt)-2-ClTrt resin, Novabiochem), to which 14.1 µmol of Fmoc-Cys (Trt) was bound, was put in a reaction vessel of an automatic synthesizer (Shimadzu Corp.). 600 µL of DMF was added to the vessel followed by stirring for 3 min, then the solution was discharged, and the following operation was carried out according to the synthesis program of Shimadzu Corp.

(a) After adding 900 µL of 30% piperidine-DMF solution, the mixture was stirred for 4 min and the solution was discharged. This operation was repeated one more time.

(b) The carrier resin was washed for 1 min with 900 µL of DMF, then the solution was discharged. This operation was repeated five times.

(c) Fmoc-Leu-OH (141 µmol), PyBOP (141 µmol), HOBt1 hydrate (141 µmol) and NMM (212 µmol) were stirred for 3 min in DMF (494 µL) and the obtained solution was added to the resin, and the mixture was further stirred for 30 min, and the solution was discharged.

(d) The carrier resin was washed for 1 min with 900 µL of DMF, followed by the discharge of the solution. This operation was repeated five times.

Fmoc-Leu-Cys (Trt) was thus synthesized on the carrier.

Next, after the steps of (a) and (b), a condensation reaction was raised in step (c) with Fmoc-Ala-OH, and after the washing step of (d), Fmoc-Ala-Leu-Cys (Trt) was synthesized on the carrier.

Then, Fmoc-Glu(OtBu)-OH, Fmoc-Arg(Pmc)-OH, Fmoc-Glu(OtBu)-OH, Fmoc-Arg(Pmc)-OH, Fmoc-Glu(OtBu)-OH, Fmoc-Glu(OtBu)-OH, Fmoc-Glu(OtBu)-OH, Fmoc-Gln(Trt)-OH, Fmoc-Ala-OH, Fmoc-Gly-OH, Fmoc-Gly-OH, Fmoc-Trp(Boc)-OH, Fmoc-Gly-OH, Fmoc-Gly-OH, Fmoc-Glu(OtBu)-OH, Fmoc-Trp-OH, Fmoc-Glu(OtBu)-OH, Fmoc-Arg(Pmc)-OH were sequentially used in step (c), and the steps (a) to (d) were repeated. Subsequently, following the deprotection and washing steps of (a) and (b), the carrier resin was sequentially washed with methanol and butylethel and dried for 12 h under reduced pressure to obtain the carrier resin to which a peptide with unprotected N-terminal and protected side-chain is bound. Next, the carrier resin thus obtained was subjected to the following operations of (e)-(g).

(e) The carrier resin was washed for 1 min with 800 µL of DMF, and the solution was discharged. This operation was repeated three times.

(f) Acetic acid anhydride (282 µmol) and DMF (500 µL) were added to the resin, and the mixture was stirred for 2 h, followed by discharge of the solution.

(g) The carrier resin was washed for 1 min with 800 µL of DMF and the solution was discharged. This operation was repeated three times.

The resin was sequentially washed with methanol and butylethanol and dried for 12 h under reduced pressure to afford a carrier resin to which a side-chain protecting peptide with the acetylated N-terminal was bound. 1 mL of a mixed solution consisting of TFA containing 2-methylindol at a concentration of 5 mg/mL (82.5%), thioanisole (5%), water (5%), ethylmethylsulfide (3%), 1,2-ethanedithiol (2.5%) and thiophenol (2%) was added to this carrier resin and left for 6 h at room temperature, then a peptide was excised from the resin as well as the side-chain protecting group being removed. After the filtration of the resin, approximately 10 mL of ether was added to the obtained solution, and the precipitation yielded was collected by centrifugation and decantation to afford 44.6 mg of a crude peptide. The total amount of the crude product was dissolved in a mixed solution consisting of dithiothreitol and DMF, then purified by HPLC using a reversed-phase column (Shiseido Co. Ltd., CAPCELL PAK C18 30 mmI.D.×250 mm). Elution was carried out by a linear concentration gradient method in which a 90% acetonitrile aqueous solution containing 0.1% TFA was added to a 0.1% TFA aqueous solution, then the detection at 220 nm was performed, and the fraction containing Compound 1 was obtained. This fraction was freeze-dried to afford 1.6 mg of Compound 1.

Mass spectroscopy [TOFMS]; m/z=2520.7 (M+H$^+$) Amino acid analysis; Glx 7.6 (8), Gly 4.0 (4), Arg 2.9 (3), Ala 2.2 (2), Leu 1.2 (1), Cys 1.7 (1)

(2) Preparation of Immunogen

The partial peptide of human SCGF obtained in Example 1 (1) was conjugated with KLH (Calbiochem) according to the following method in order to enhance immunogenicity, and the conjugate was used as an immunogen. More specifically, KLH is dissolved in PBS such that the solution was in a final concentration of 10 mg/mL, and 1/10 volume of 25 mg/mL MBS (Nakalai Tesque, Inc.) was added thereto dropwise. Then, the mixture was stirred for 30 min for reaction. Free MBS was removed by subjecting the reaction mixture to a gel filtration column such as a Sephadex G-25 column that had been counterbalanced with PBS beforehand, and 2.5 mg of KLH-MB obtained as a result was mixed with 1 mg of a peptide dissolved in a 0.1 mol/L sodium phosphate buffer (pH 7.0), which was stirred for 3 h at room temperature for reaction. After the reaction, the mixture was dialyzed with PBS.

(3) Immunization of Animals and Preparation of Antibody-producing Cells

Five-week-old female rats (SD) were administered 100 μg of the peptide-KLH conjugate prepared in Example 1 (2) together with 2 mg aluminum gel and 1×10$^9$ cells of pertussis vaccine (Chiba Serum Institute). From 2 weeks after the administration, 100 μg of the conjugate was administered to the rats once a week for the total of four times. Blood was collected from the venous plexus in ocular fundus, and the serum antibody titers were examined by an enzyme-linked immunosorbent assay as shown in the following section (4). Then the spleens were excised from rats that exhibited sufficient antibody titers 3 days after the final immunization.

The spleens were chopped in a MEM medium (Nissui Pharmaceutical Co., Ltd.), loosened with a forcep and subjected to centrifugation (1,200 rpm, 5 min). Upon removing the supernatants, the spleens were treated with a Tris-ammonium chloride buffer (pH 7.65) for 1-2 min to remove erythrocytes and washed three times in a MEM medium and then provided as splenocytes for use in the cell fusion.

(4) Enzyme-linked Immunosorbent Assay (Binding ELISA)

A conjugate of the partial peptide of human SCGF obtained in Example 1 (1) and thyroglobulin (hereinafter abbreviated as THY) was used as an assay antigen. Method for preparing the conjugate is the same as described in Example 1 (2) except that SMCC (Sigma Corp.) was used instead of MBS as a cross-linking agent. The conjugate prepared as above was pipetted to a 96-well EIA plate (Greiner Bio-One) at 10 μg/mL and 50 μL/well and placed overnight at 4° C. to allow the conjugate to be absorbed. After the plate being washed, 1% BSA-PBS was added at 100 μL/well, and the reaction was raised for 1 h at room temperature to block the remaining active group. 1% BSA-PBS was discarded, then anti-serum of the immunized mice, culture supernatant of the anti-human SCGF monoclonal antibody, or a purified monoclonal antibody was pipetted at 50 μL/well, and reaction was raised for 2 h. After washing with tween-PBS, the peroxidase-labeled rabbit anti-rat immunoglobulin (DAKO Corp.) was added at 50 μL/well, and reaction was raised for 1 h at room temperature. After washing with tween-PBS, an ABTS substrate solution [2.2-azinobis (3-ethylbenzothiazol-6-sulfonate) ammonium] was used for color development, then the absorbance at OD415 nm was measured with a plate reader (E-max; Molecular Devices).

(5) Preparation of Mouse Myeloma Cells

P3-U1, the 8-azaguanine-resistant mouse myeloma cell line, was cultured in a normal medium, and 2×10$^7$ or more cells were reserved at the time of cell fusion and provided as a parent line for fusing the cells.

(6) Production of Hybridoma

Rat splenocytes obtained in Example 1 (3) and myeloma cells obtained in (5) were mixed at the ratio of 10:1 and subjected to centrifugation (1,200 rpm, 5 min). The supernatant was then discarded, and the precipitated cells were well loosened, then a mixed solution composed of polyethylene glycol-1000 (PEG-1,000) (2 g), MEM medium (2 mL) and dimethyl sulphoxide (0.7 mL) was added at 0.2-1 mL per 10$^8$ rat splenocytes under stirring at 37° C. MEM medium was added by 1-2 mL for several times every 1-2 min, then MEM medium was further added to make the total amount 50 mL. After the centrifugation (900 rpm, 5 min), the supernatant was discarded, and the cells were gently loosened. These cells were then drawn in a measuring pipette and blown out in a 100 mL HAT medium to allow gentle suspension.

This suspension was pipetted to a 96-well culture plate at 100 μL/well and cultured in a 5% CO$_2$ incubator for 10 to 14 days at 37° C. The culture supernatant was examined by an enzyme-linked immunosorbent assay described in Example 1 (4) to select wells that react to a partial peptide of human SCGF (Compound 1) but that do not react to another partial peptide of SCGF, i.e. a peptide consisting of 140-156 amino acids within SEQ. ID No. 1. Further, the medium was replaced by a HT medium and a normal medium, and cloning was repeated twice to establish the anti-human SCGF monoclonal antibody-producing hybridomas; KM2141, KM2142, KM2143, KM2144 and KM2145.

(7) Purification of Monoclonal Antibodies

The hybridoma lines obtained in Example 1 (6) were intraperitoneally injected into 8-week-old nude female mice (Balb/c) that had been treated with Pristane at 5-20×10$^6$ cells per mouse. The hybridomas turned into ascites tumor 10 to 21 days after the injection. Ascitic fluid was collected from the mice accumulating ascitic fluid (1-8 mL/mouse), and the solid was removed by centrifugation (3,000 rpm, 5 min). When IgM was adopted as a monoclonal antibody, salting out was carried out with 50% ammonium sulfate and dialysis was carried out with PBS which had been added 0.5 M sodium chloride. The IgM fraction was then collected by passing through a Cellurofine GSL2000 column (SEIKAGAKU CORPORATION) (bed volume of 750 mL) at a flow rate of 15 mL/h to give a purified monoclonal antibody. When IgG was adopted as a monoclonal antibody, purification was carried out by the caprylic acid precipitation [Antibodies—A Laboratory Manual, Cold Spring Harbor Laboratory (1988)] to give a purified monoclonal antibody.

Subclasses for the antibodies were determined by an enzyme-linked immunosorbent assay using a subclass typing kit (Table 1).

TABLE 1

| Antibody | Antibody class |
|---|---|
| KM2141 | G2a |
| KM2142 | G2a |
| KM2143 | G2a |
| KM2144 | G2a |
| KM2145 | G1 |

(8) Reactivity to a Partial Peptide of Human SCGF (Enzyme-Linked Immunosorbent Assay)

Figure 1:
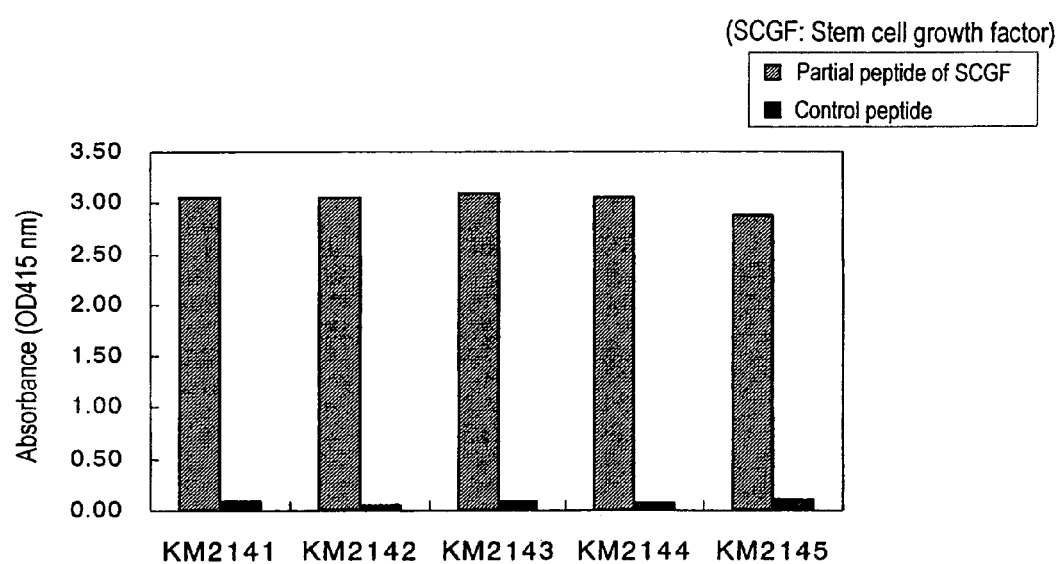
FIG. 1 shows the reactivity of monoclonal antibodies to a partial peptide of human SCGF (Compound 1) (Binding ELISA).

The reactivity of the anti-human SCGF monoclonal antibodies selected in Example 1 (6) to the partial peptide of human SCGF (Compound 1) was examined by an enzyme-linked immunosorbent assay described in (4). A peptide comprising an amino acid sequence of 140-156 amino acids in SEQ. ID No. 1, being a partial peptide of SCGF different from Compound 1, was used as a control peptide. As shown in FIG. 1, the anti-human SCGF-monoclonal antibodies (KM2141-2145) specifically reacted to Compound 1 but not to a control peptide.

Example 2

Expression and Purification of Human SCGF with the Use of Animal Cells (1) Construction of pAGE-SCGFα, the Human SCGF-Expressing Plasmid, and the Expression of Human SCGF in Animal Cells A fragment of pAGE210 (WO96/34016), an expression vector for animal cells, which is treated with HindIII/KpnI, was bound to DNA encoding SCGF protein [Mio et. al., BBRC 249, 124-130 (1998)] to construct pAGE-SCGFα, a human SCGF-expressing vector.

The plasmid was introduced into animal cells by an electroporation method according to the method of Miyaji et al. [Miyaji et al., Cytotechnology, 3, (underlining in original) 133-140 (1990)]. 4 μg of pAGE-SCGF-a was introduced into $4 \times 10^6$ cells of the dhfr gene-deficient CHO cell line [Urlaub and Chasin, Proc. Natl. Acad. Sci. USA, 77, (underlining in original) 4216-4220 (1980)]. These cells were suspended in 10 mL MEMa2000-dFCS(5) medium MEMa2000 medium (GIBCO/BRL) containing 5% dFCS, 1/40 volume of 7.5% $NaHCO_3$, 200 mL of 3% glutamine solution (GIBCO/BRL), and 0.5% penicillin/streptomycin solution (GIBCO/BRL, containing 5,000 units/mL penicillin and 5,000 mg/mL streptomycin)], then placed in a 10-cm plate (IWAKI & Co. Ltd.), and cultured in a $CO_2$ incubator under 37° C. for 24 h. Hygromycin (GIBCO/BRL) was added thereto to the final concentration of 0.3 mg/mL, and the cells were further cultured for 1 to 2 weeks. The cells were collected when the transformant cells become confluent, suspended in MEMa2000-dFCS(5) medium containing 0.3 mg/mL of hygromycin and 50 nmol/L of methotrexate (MTX) at $1-2 \times 10^6$ cells/mL, and then pipetted to F75 flasks (Greiner) by 2 mL. After cultivation for 1 to 2 weeks, those cells resistant to 50 nmol/L MTX were suspended in MEMa2000-dFCS(5) medium containing 0.3 mg/mL hygromycin and 200 nmol/L MTX at $1-2 \times 10^5$ cells/mL, and pipetted to F75 flasks (Greiner) by 2 mL. After cultivation for 1 to 2 weeks, the cells resistant to 200 nmol/L MTX were obtained. These cells resistant to 200 nmol/L MTX were cultured in a 2 L-roller bottle (Greiner) at 37° C. and 80 rounds/min by using the medium 1) and medium 2) shown below.

Medium 1) Ex-cell 301 serum-free medium (JRH Biosciences).

Medium 2) Ex-cell 301 serum-free medium containing 10 mg/L aprotinin (Sigma).

After the cultivation for about 5 days, the cells were subjected to centrifugation, and the culture supernatant samples were obtained.

(2) Confirmation of the Presence of SCGF Protein in the Culture Supernatant by Western Blotting Using the Monoclonal KM2142 Antibody The presence of SCGF protein in the culture supernatant obtained in the above-described (1) was examined by western blotting using the anti-human SCGF monoclonal KM2142 antibody obtained in Example 1, by the method described below.

After the SDS-PAGE separation of each purified fraction that had been obtained by purifying SCGF protein through chromatography as described (3) and (4) below, the fractions were electronically transferred onto a PVDF membrane (Immobilon Tansfer Membranes, Millipore) according to the method of P. Matsudaira [J. B. C. 262, 10035-10038 (1987)]. The transferred membrane was shaken for 30 min in a blocking solution [PBS buffer (137 mmol/L NaCl, 2.7 mmol/L KCl, 9.6 mmol/L $Na_2HPO_4/KH_2PO_4$ (pH 7.2)) containing 1% BSA], followed by shaking for 60 min at room temperature in a solution containing an anti-SCGF monoclonal antibody diluted to 1 mg/mL with the blocking solution. This transcribed membrane was further washed twice for 5 min with a PBS buffer containing 0.05% tween20, washed once for 5 min with PBS buffer, then shaken for 60 min at room temperature in a solution containing the peroxidase-labeled anti-rat IgG antibody (anti-rat immunoglobulin 1.3 g/L, DAKO Corp.) diluted to 1/1000 with PBS. Washing was carried out twice each for 5 min in PBS buffer containing 0.05% tween20, and further once for 5 min in PBS buffer, then the detection was carried out by a luminescent method (ECL Western blotting detection reagents, Amersham Pharmacia Biotech).

(3) Purification of a Human SCGF Protein from the Culture Supernatant of CHO Cells For producing the anti-human SCGF monoclonal antibodies described in Example 3, the purified human SCGF protein was obtained by the following two-step chromatography from the culture supernatant of CHO cells obtained under the culture conditions of the medium 1) described in the above-mentioned (1).

Step 1: Zinc Chelate Chromatography

The Chelating Sepharose Fast Flow carrier saturated with $Zn^{2+}$ ion (Amersham Pharmacia Biotech) was filled in a 2.5 cm ø×20 cm column (BioRad) to the height of 11 cm and equilibrated with 20 mmol/L of the sodium phosphate buffer containing 0.5 mol/L sodium chloride (pH 7.1). 2.4 L of the culture supernatant of CHO cells obtained in the above-described (1) was added to the column, which was washed well with the above-mentioned buffer, and eluted by the linear concentration gradient with 0-100 mmol/L histidine. SDS-PAGE was carried out about a part of the eluted fraction, and the fraction including a crossed band of approximately 45 kDa was collected by western blotting using KM2142 shown in the above-described (2).

Step 2: MonoQ Anion-exchange Chromatography

Figure 2:
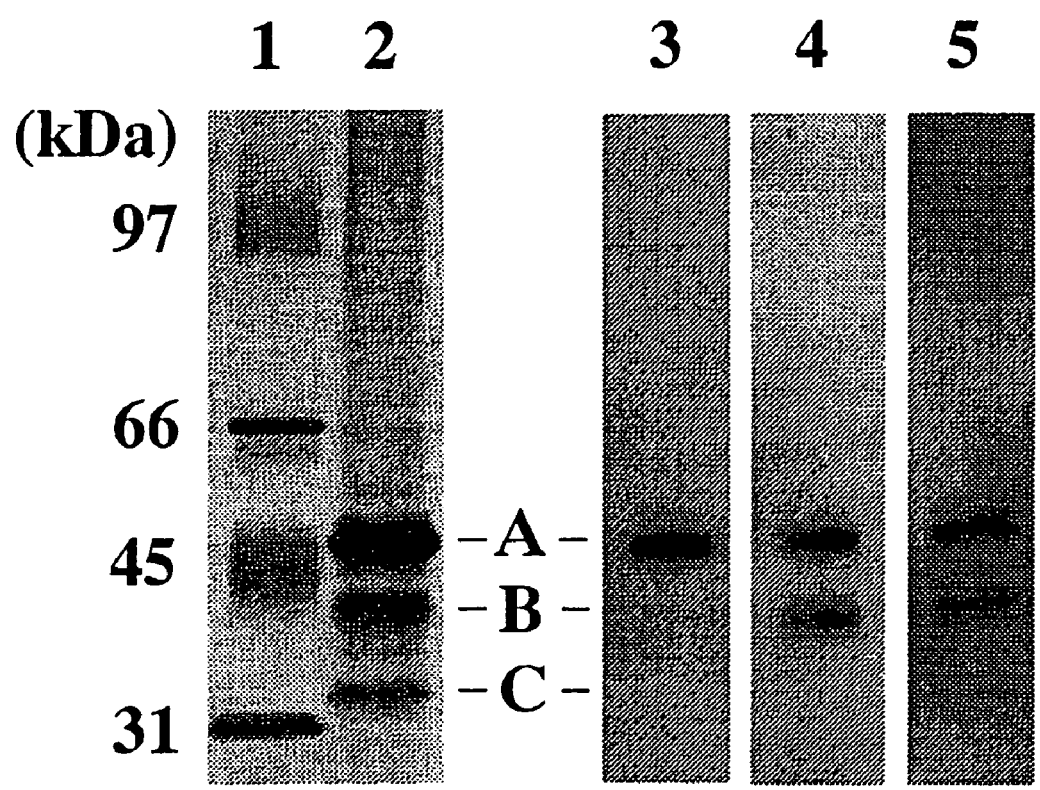
FIG. 2 shows the results of SDS-PAGE and western blotting for the purified human SCGF protein. Lanes 1 and 2 show SDS-PAGE patterns of a molecular weight marker and the purified human SCGF protein. Lanes 3, 4 and 5 indicate the results of western blotting for the purified human SCGF protein using KM2142, KM2804 and KM2945, respectively.

Ammonium sulfate was added at a final concentration of 65% to the fraction that had been crudely purified by the above-mentioned zinc chelate chromatography. The mixture was stirred and left for 2 h at 4° C. The precipitate obtained by the centrifugation at 18,800×g for 30 min was dissolved in a 10 mmol/L tris-HCl buffer (pH 7.0), and added to a MonoQ HR 5/5 column (Amersham Pharmacia Biotech) equilibrated with the tris-HCl buffer. The column was then well washed with the above-mentioned tris-HCl buffer, and eluted by the linear concentration gradient with 0-1 mol/L sodium chloride. SDS-PAGE was carried out about a part of the eluted fraction and the fraction including a crossed band of approximately 45 kDa was collected by western blotting using monoclonal KM2142 antibody shown in the above-described (2) (FIG. 2, Lane 2).

(4) High-purity Purification for the Human SCGF Protein From the Culture Supernatant of CHO Cells The culture supernatant of CHO cells obtained under the culture conditions of the medium 2) described in the above-mentioned (1) was subjected to purification by the following three-step chromatography to obtain a standard substance for the human SCGF protein for use in a quantification system for the human SCGF protein as described in Example 6.

Step 1: Zinc Chelate Chromatography

The Chelating Sepharose Fast Flow carrier saturated with $Zn^{2+}$ ion (Amersham Pharmacia Biotech) was filled in a 5.0 cm ø×20 cm column (BioRad) to the height of 14.5 cm and equilibrated with 20 mmol/L of the sodium phosphate buffer containing 0.5 mol/L sodium chloride (pH 7.1). 12 L of the culture supernatant of CHO cells obtained in the above-described (1) was added to the column, which was washed well with the above-mentioned buffer, and eluted by the linear concentration gradient with 0-100 mmol/L histidine. SDS-PAGE was carried out about a part of the eluted fraction, and the fraction including a crossed band of approximately 45 kDa was obtained by western blotting using KM2142 shown in the above-described (2).

Step 2: MonoQ Anion-exchange Chromatography

Ammonium sulfate was added to the final concentration of 50% to the fraction which had been crudely purified by the above-mentioned zinc chelate chromatography. The mixture was stirred and left for 2 h at 4° C. The precipitate obtained by the centrifugation at 18,800 g for 30 min was dissolved in a 10 mmol/L tris-HCl buffer (pH 7.0), which was then added to a MonoQ HR 10/10 column (Amersham Pharmacia Biotech) equilibrated with the tris-HCl buffer. The column was then washed well with the above-mentioned tris-HCl buffer, and eluted by the linear concentration gradient with 0-1 mol/L sodium chloride. SDS-PAGE was carried out about a part of the eluted fraction, and the fraction including a crossed band of approximately 45 kDa was collected by western blotting using KM2142 shown in the above-described (2).

Step 3: S-400 Gel Filtration Chromatography

XK50/60 column (Amersham Pharmacia Biotech) filled with a Sephacryl S-400 HR carrier (Amersham Pharmacia Biotech) to the height of 51.5 cm was serially connected with XK50/100 column (Amersham Pharmacia Biotech) filled with the same carrier to the height of 93 cm. The columns were well equilibrated with PBS buffer, and 28 mL of the fraction that had been purified by the above-described MonoQ anion-exchange chromatography was added thereto, which was subjected to elution with PBS buffer at a flow rate of 6 mL/min. SDS-PAGE was carried out about a part of the eluted fraction, and the fraction including a crossed band of approximately 45 kDa was collected by western blotting using the monoclonal KM2142 antibody shown in the above-described (2).

(5) Analysis for the N-terminal Amino Acid Sequence of the Human SCGF Protein

The N-terminal amino acid sequence in the purified human SCGF protein obtained in Example 2 (3) was determined according to a common protocol in protein chemistry. A fraction including the purified human SCGF protein was subjected to SDS-PAGE and silver-stained (FIG. 2, Lane 2) or electrically transferred onto a PVDF membrane (ProBlott, Applied Biosystems) by the method of P. Matsudaira. The transferred membrane was stained with Coomassie blue, and the bands with apparent molecular weights of 45 kDa (FIG. 2, Lane 2, Band A), 41 kDa (FIG. 2, Lane 2, Band B) and 34 kDa (FIG. 2, Lane 2, Band C) were excised, and the amino acid sequence for each was determined with a gas-phase protein sequencer (PPSQ-10, Shimadzu Corp.) according to the method recommended by the manufacturer. The obtained amino acid sequences were the sequences shown by SEQ ID Nos. 5, 6 and 7, respectively, which were identical with the amino acid sequences each starting from the first amino acid residue, the 29th amino acid residue and 60th amino acid residue from the N-terminal in the SCGF amino acid sequence shown by SEQ. ID No. 1. The SCGF protein with the approximate apparent molecular weight of 41 kDa shown in Lane 2 in FIG. 2 with the deletion of its 28th residue on the N-terminal is named Δ28, and that with the approximate apparent molecular weight of 34 kDa with the deletion of its 59th residue on the N-terminal is named Δ59, hereinafter.

Example 3

Production of the Anti-human SCGF Monoclonal Antibodies by Using the CHO Cell-expressing Human SCGF Protein (1) Immunization of Animals and Preparation of the Antibody-Producing Cells 100 μg of the CHO cell-expressing human SCGF protein obtained in Example 2 (3) (a SCGF mixture consisting of SCGF, Δ28 and Δ59) was administered to the 6-week-old female mice (Balb/c) together with 2 mg of aluminum gel and $1×10^9$ cells of pertussis vaccine (Chiba Serum Institute). Commencing 2 weeks after this administration, 100 μg of the human SCGF protein was administered once a week for the total of three times. Blood was collected from the venous plexus in ocular fundus, and the serum antibody titers were measured by an enzyme-linked immunosorbent assay (the CHO cell-expressing human SCGF protein was used as an assay antigen and 1% BSA-PBS was used as a control antigen) and by the sandwich ELISA method shown below. The spleens that exhibited sufficient antibody titers were excised from the mice 3 days after the final immunization.

Antibody-producing cells were prepared by a similar manner as in Example 1 (3).

(2) Sandwich ELISA Method

The anti-human SCGF monoclonal antibody, KM2142, obtained in Example 1 was pipetted to a 96-well EIA plate (Greiner Bio-One) at 10 μg/mL and 50 μL/well, and left overnight at 4° C. to allow the antibody to be absorbed. After washing the plate, 1% BSA-PBS was added at 100 μL/well, which was subjected to reaction for 1 h at room temperature to block any remaining active group. The 1% BSA-PBS was discarded, and the CHO cell-expressing human SCGF protein which was diluted with 1% BSA-PBS to 50 µL/mL was pipetted at 50 µL/well, which was subjected to reaction for 2 h at room temperature. 1% BSA-PBS was pipetted at 50 µL/well as a control, which was subjected to reaction in a similar manner. After washing with Tween-PBS, the culture supernatant of the immunized mouse anti-serum obtained in the above (1) was pipetted at 50 µL/well, which was subjected to reaction for 2 h. After washing with Tween-PBS, the peroxidase-labeled anti-mouse immunoglobulin (absorbing the rat serum protein in advance; CALTAG) was added at 50 µL/well, which was subjected to reaction for 1 h at room temperature. After washing with Tween-PBS, an ABTS substrate solution [2.2-azinobis (3-ethylbenzothiazol-6-sulfonate) ammonium] was added for color development, and the absorbance at OD415 nm was measured with a plate reader (Emax; Molecular Devices).

(3) Preparation of Mouse Myeloma Cells

The cells were prepared similarly as in Example 1 (5).

(4) Production of Hybridoma

Mouse spleen cells obtained in Example 3 (1) and myeloma cells obtained in (3) were subjected to cell fusion in a similar manner as in Example 1 (6).

The cell suspension obtained was pipetted to a 96-well culture plate at 100 µL/well and cultured in a 5% $CO_2$ incubator for 10 to 14 days at 37° C. This culture supernatant was examined by the sandwich ELISA method described in Example 3 (2), and the wells responsive to the human SCGF protein but unresponsive to the control 1% BSA-PBS were selected. Further, the medium was replaced by a HT medium and normal medium, cloning was repeated twice, and the anti-human SCGF monoclonal antibody-producing hybridomas, KM2801, KM2802, KM2803 and KM2804 were established.

(5) Purification of Monoclonal Antibodies

Hybridoma lines obtained in Example 3 (4) were intraperitoneally administered to nude female mice in a similar manner as in Example 1 (7), and the purified monoclonal antibodies were obtained from the ascitic fluid.

The subclasses of the antibodies were determined by an enzyme-linked immunosorbent assay using a subclass typing kit. The results are shown in Table 2.

TABLE 2

| Antibody | Antibody class |
| --- | --- |
| KM2801 | G1 |
| KM2802 | G1 |
| KM2803 | G1 |
| KM2804 | G1 |

(6) Reactivity to the CHO Cell-expressing Human SCGF Protein (Enzyme-linked Immunosorbent Assay)

The reactivity of the anti-human SCGF monoclonal antibodies obtained in Example 3 (4) to the CHO cell-expressing human SCGF protein was examined by an enzyme-linked immunosorbent assay described in Example 1 (4). As shown in FIG. 3, the anti-human SCGF monoclonal antibodies (KM2801, KM2802, KM2803 and KM2804) specifically reacted to the CHO cell-expressing human SCGF protein but did not to the control 1% BSA-PBS.

Example 4

Production of the Anti-human SCGF Monoclonal Antibodies by Using the SDS-denatured Human SCGF Protein (Expressed by CHO Cells)

When the undenatured human SCGF protein described in Example 3 was used as an immunogen, no monoclonal antibody reacting with Δ59 was obtained. Accordingly, in order to produce a monoclonal antibody reacting with Δ59, a hybridoma was prepared using the SDS-denatured SCGF as an antigen.

(1) Preparation of an Immunogen

An immunogen was prepared by denaturing the CHO cell-expressing human SCGF protein obtained in Example 2 (3) by the addition of SDS (sodium dodecyl sulfate; Nacalai Tesque, Inc.). More specifically, 5% SDS-PBS was prepared, and the 1/9 volume was added to the CHO cell-expressing human SCGF protein, which was then boiled at 100° C. for 5 min, and thus the SDS-denatured human SCGF protein was provided.

(2) Immunization of Animals and Preparation of Antibody-producing Cells

Six-week-old female mice (Balb/c) were administered 100 µg of the SDS-denatured human SCGF protein prepared in Example 4 (1) together with aluminum gel (2 mg) and pertussis vaccine ($1 \times 10^9$ cells) (Chiba Serum Institute). Commencing 2 weeks after this administration, 100 µg of the SDS-denatured human SCGF protein was administered to the mice once a week for the total of three times. Blood was collected from the venous plexus in ocular fundus, and the serum antibody titers were measured by an enzyme-linked immunosorbent assay as shown in Example 1 (4) (SDS-denatured human SCGF protein was used as an assay antigen and 1% BSA-PBS was used as a control antigen). Then, the spleens were excised from the mice which exhibited sufficient antibody titers 3 days after the final immunization.

Antibody-producing cells were prepared in a similar manner as in Example 1 (3).

(3) Preparation of Mouse Myeloma Cells

The cells were prepared in a similar manner as described in Example 1 (5).

(4) Production of Hybridomas

The mouse myeloma cells obtained in Example 4 (2) and the myeloma cells obtained in (3) were subjected to cell fusion in a similar manner as in Example 1 (6).

The cell suspension obtained was pipetted to a 96-well culture plate by 100 µL/well and cultured in a 5% $CO_2$ incubator for 10 to 14 days at 37° C. This culture supernatant was examined by the enzyme-linked immunosorbent assay described in Example 1 (4), and the wells responsive to the SDS-denatured human SCGF protein but unresponsive to the control 1% BSA-PBS were selected. Further, the medium was replaced by a HT medium and normal medium, cloning was repeated twice, and the anti-human SCGF monoclonal antibody-producing hybridomas, KM2941, KM2942, KM2943, KM2944 and KM2945 were established.

(5) Purification of Monoclonal Antibodies

The hybridoma lines obtained in Example 4 (4) were intraperitoneally administered to nude female mice in a similar manner as in Example 1 (7), and the purified monoclonal antibodies were obtained from the ascitic fluid.

The subclasses of the antibodies were determined by an enzyme-linked immunosorbent assay using a subclass typing kit. The results are shown in Table 3.

TABLE 3

| Antibody | Antibody class |
|---|---|
| KM2941 | G1 |
| KM2942 | G1 |
| KM2943 | G1 |
| KM2944 | G1 |
| KM2945 | G1 |

(6) Reactivity to the SDS-denatured Human SCGF Protein (Enzyme-linked Immunosorbent Assay)

Reactivity of the anti-human SCGF monoclonal antibodies obtained in Example 4 (4) to the SDS-denatured human SCGF protein was examined by the enzyme-linked immunosorbent assay described in Example 1 (4). As shown in FIG. 4, the anti-human SCGF monoclonal antibodies (KM2941, KM2942, KM2943, KM2944 and KM2945) specifically reacted to the SDS-denatured human SCGF protein but did not react to the control 1% BSA-PBS.

Example 5

Study of Reactivity of the Anti-human SCGF Monoclonal Antibodies (1) Reactivity to the Human and Mouse SCGF Proteins Reactivity of the anti-human SCGF monoclonal antibodies produced in Examples 1, 3 and 4 to the human and mouse SCGF proteins were examined by an enzyme-linked immunosorbent assay (binding ELISA). The mouse SCGF protein was produced in accordance with the method described in Example 2.

The CHO cell-expressing human and mouse SCGF proteins were used as assay antigens, and the assay was conducted according to the method described in Example 1 (4). The results are shown in FIG. 5.

An anti-SCGF monoclonal KM2142 antibody is a hybridoma-derived antibody prepared by using a partial peptide corresponding to the 6-25 residues on the N-terminus of the SCGF amino acid sequence shown by SEQ. ID No. 1 (Compound 1) as an antigen. The anti-SCGF monoclonal KM2142 antibody has been shown to possess reactivity to SCGF protein as well. The anti-SCGF monoclonal KM2142 antibody has been further shown to possess reactivity to both human and mouse SCGF proteins.

An anti-SCGF monoclonal KM2804 antibody is a hybridoma-derived antibody prepared by using the CHO cell-expressing human SCGF protein as an antigen. The anti-SCGF monoclonal KM2804 antibody exclusively reacts to human SCGF and did not exhibit cross-reactivity to mouse SCGF.

An anti-SCGF monoclonal KM2945 antibody is a hybridoma-derived antibody produced by using the SDS-denatured SCGF protein (expressing CHO cells) as an antigen. The anti-SCGF monoclonal KM2945 antibody has been shown to possess reactivity to undenatured SCGF protein as well. The anti-SCGF monoclonal KM2945 antibody did not exhibit cross-reactivity to mouse SCGF.

(2) Western Blotting

KM2804 and KM2945, the anti-human SCGF monoclonal antibodies prepared in Examples 3 and 4 were studied for their reactivity in western blotting, using the CHO cell-expressing human SCGF protein obtained in Example 2 (3).

A sample transferred onto a PVDF membrane in a similar manner as in Example 2 (2) was shaken in a blocking solution for 30 min at room temperature, and subsequently shaken for 60 min at room temperature in a solution of anti-SCGF monoclonal antibody diluted with a blocking solution to 1 mg/mL. The transferred membrane was further washed twice for 5 min with a PBS buffer containing 0.05% Tween20, once for 5 min with a PBS buffer, and was further shaken for 60 min at room temperature in a solution of peroxidase-labeled anti-mouse IgG antibody (Amersham Pharmacia Biotech) diluted with PBS to 1/1000. Washing was carried out twice for 5 min with a PBS buffer containing 0.05% Tween20, once for 5 min in a PBS buffer, then the detection was carried out with the ECL luminescence method as above described.

Lanes 3, 4 and 5 in FIG. 2 represent the results of western blotting for the purified human SCGF proteins using KM2142, KM2804 and KM2945, respectively. Although KM2804 did not possess reactivity to Δ59 which is a SCGF protein lacking the 59th residue from the N-terminus, it possessed reactivity to Δ28 which is a SCGF protein lacking the 28th residue from the N-terminus. KM2945 possessed reactivity to both the full-length and deletion-type SCGFs.

Example 6

Determination System for Human SCGF

An anti-human SCGF monoclonal KM2142 antibody obtained in Example 1 was biotin-labeled by the following procedure. The purified KM2142 antibody obtained in Example 1 was diluted with PBS to 1 mg/mL, and 1/4 volume of 0.5 mol/L carbonate buffer (pH 9.2) was added thereto. Then NHS-Lc-Biotin (dissolved to 1 mg/mL with dimethylformamide; Pierce Biotechnology, Inc.) was added dropwise under stirring in the amount equal to the buffer. The mixture was stirred for 3 h at room temperature for reaction followed by dialysis with PBS overnight, and the resultant was used as a biotin-labeled KM2142.

An anti-human SCGF monoclonal KM2804 antibody obtained in Example 3 was pipetted to a 96-well EIA plate (Greiner) at 5 μg/mL and 50 μL/well, and the plate was left overnight at 4° C. to allow the antibody to be adsorbed. After washing the plate, 1% BSA-PBS was added at 100 μL/well, which was subjected to reaction for 1 h at room temperature to block any remaining active group. The 1% BSA-PBS was discarded, then the CHO cell-expressing human SCGF protein obtained in Example 2 (4), which was diluted with a serum dilution solution (Kyowa Medex Co., Ltd.) 14 times in two-fold dilution line starting from 17.5 ng/mL, was pipetted at 50 μL/well and allowed to react for 2 h at room temperature. After washing with Tween-PBS, the biotin-labeled KM2142 obtained above (diluted to 0.2 μg/mL with BSA-PBS) was added at 50 μL/well, which was subjected to reaction for 2 h at room temperature. After washing with Tween-PBS, alkaline phosphatase-labeled avidin (Zymed Laboratories, Inc.) was further added at ×32,000 dilution at 50 μL/well, which was subjected to reaction for 1 h at room temperature. After washing with Tween-PBS, AmpliQ (DAKO Corp.) was added thereto for color development, and the absorbance at OD490 nm was measured with a plate reader (E-max; Molecular Devices). The results revealed that the determination system of the present invention enabled quantification the human SCGF protein in a range of 0.04-2.0 ng/mL as shown in FIG. 6.

Example 7

Serum SCGF Concentration of the Patients of Leukemia, Pre-Leukemia and Aleukemic Malignant Blood Diseases The SCGF concentrations of sera from patients with informed consent and who suffer leukemia, pre-leukemia or a leukemic malignant blood diseases were determined by the method of Example 6. Ten healthy individuals, both men and women, who exhibited normal test levels in the blood cell test served as control examples, and their serum SCGF concentrations were also determined. The results are shown in FIG. 7.

Upon confirming that the levels of normal individuals fall within regular distribution, the mean value and the standard deviation (SD) were calculated for this group, and the value of "mean value+2SD" was set as a standard value to distinguish between normal and abnormal. The values of patients suffering leukemia, pre-leukemia or an aleukemic malignant blood disease were sorted based on this standard value, and whether patients of leukemia, pre-leukemia and aleukemic malignant blood diseases are detectable or not from the measured SCGF values was examined. The results are shown in Table 4.

TABLE 4

|  | Patients | Positive patients | Positive rate (%) |
|---|---|---|---|
| ALL | 7 | 7 | 100.0 |
| AML | 7 | 6 | 85.7 |
| CML | 6 | 6 | 100.0 |
| MDS | 5 | 5 | 100.0 |
| NHL | 7 | 6 | 85.7 |
| MM | 6 | 4 | 66.7 |
| AA | 7 | 0 | 0.0 |

Cut-off value was set as; the mean value of normal individuals + 2SD = 18.2 ng/mL.

The medians of the patients suffering acute myeloid leukemia (AML), acute lymphoid leukemia (ALL), chronic myeloid leukemia (CML), myelodysplastic syndrome (MDS), non-Hodgkin's lymphoma (NHL) and multiple myeloma (MM) were significantly higher than those of healthy individual group, demonstrating that measured SCGF values in these diseases had been significantly elevated (FIG. 7).

It was also demonstrated that patients with leukemia, pre-leukemia or aleukemic malignant blood diseases can be detected at a high sensitivity with the use of a cut-off value set down from the values for healthy individuals (Table 4). On the other hand, in spite of being a blood disease as well, no significant difference was observed between the values for patients with aplastic anemia (AA) and healthy individuals, and this disease was not detectable even with the use of a cut-off value.

Comparison among non-Hodgkin's lymphoma (NHL), multiple myeloma (MM), myelodysplastic syndrome (MDS), acute myeloid leukemia (AML), acute lymphoid leukemia (ALL) and chronic myeloid leukemia (CML) that accompany abnormality in the blood cell counts revealed that the blood SCGF concentrations of leukemia patients suffering such as acute myeloid leukemia (AML), acute lymphocytic leukemia (ALL) and chronic myeloid leukemia (CML) were significantly higher than those of patients suffering other pre-leukemia or aleukemic malignant blood diseases such as non-Hodgkin's lymphoma (NHL), multiple myeloma (MM) and myelodysplastic syndrome (MDS). Therefore, the blood SCGF concentration was available for discriminating leukemia, pre-leukemia or aleukemic malignant blood diseases. Further, comparison between AA and MDS patients that are difficult to discriminate and diagnose revealed that blood SCGF concentrations of MDS patients were significantly higher than those of AA patients so that it was enabled to discriminate and diagnose the patients of both diseases.

Example 8

Occurrence of Graft Versus Host Disease (GVHD) after Transplantation of the Hematopoietic Stem Cells and SCGF Concentration Among 23 cases for leukemia and pre-leukemia patients with informed consent who underwent transplantation of the hematopoietic stem cells, 15 cases that occurred GVHD and 8 cases that did not were measured for the serum SCGF concentration in each phase according to the method of Example 6. The results are shown in FIG. 8.

SCGF concentrations of the patients who underwent transplantation of the hematopoietic stem cells exhibited significantly higher levels at recovery and stable phases compared to those at pre-conditioning and aplastic phases.

Among the patients who underwent transplantation of the hematopoietic stem cells, cases with the occurrence of GVHD exhibited significantly higher serum SCGF concentrations in aplastic and recovery phases compared to those in the cases without occurrence of the disease. Thus, the occurrence of GVHD was diagnosed by measuring the serum SCGF concentration.

Further, study was made as to the possibility of diagnosing the cases with and without the occurrence of GVHD by setting the cut-off value. The results are shown in FIG. 9. In pre-conditioning phase, by setting the cut-off value, for instance, at 5 ng/mL, SCGF concentration was measured with sensitivity of 87% and specificity of 57%; in aplastic phase, with sensitivity of 87% and specificity of 63% by setting the cut-off value at 10 ng/mL; and in recovery phase, with sensitivity of 87% and specificity of 63% by setting the cut-off value at 15 ng/mL. Consequently, it was possible to significantly ($p<0.05$) discriminate the cases with or without the occurrence of GVHD compared to the diagnosis without the use of the cut-off values.

Example 9

Engraftment of Transplanted Hematopoietic Stem Cells and the Serum SCGF Concentration Among 23 cases of patients suffering blood diseases with informed consent who underwent transplantation of the hematopoietic stem cells, the serum SCGF concentrations of 4 cases with delayed engraftment and 19 cases without delayed engraftment were measured in each phase by using the method of Example 6. The results are shown in FIG. 10.

In the cases without delayed engraftment, the SCGF concentrations at recovery and stable phases rose significantly compared to those in pre-conditioning phase. While in the cases with delayed engraftment, any significant rise in the concentrations was not observed even in these phases.

Therefore, it was examined whether the cases with and without delayed engraftment of the hematopoietic stem cells can be diagnosed by measuring SCGF concentrations of the patients who underwent transplantation of the hematopoietic stem cells and by setting down a cut-off value and comparing the value of each patient with the cut-off value. The results are shown in FIG. 11. In pre-conditioning phase, by setting the cut-off value, for instance, at 9.5 ng/mL, cases with and without delayed engraftment of the hematopoietic stem cells were diagnosed with sensitivity of 75% and specificity of 67% and in aplastic phase, with sensitivity of 75% and specificity of 63% by setting the cut-off value at 12 ng/mL. Consequently, it was possible to significantly diagnose the cases with and without delayed engraftment of the hematopoietic stem cells.

Example 10

Expression of SCGF in the Peripheral Blood Cells of Leukemia Patients

Peripheral blood cells of various leukemia patients with informed consent were subjected to treatment with Rneasy Mini Kit (Qiagen) according to the protocol to extract total RNA. Then 1 µg of the total RNA was treated with DNaseI (GIBCO), reversely transcribed using SuperScript First-Strand Synthesis System for RT-PCR (GIBCO), and thus First-Strand DNA was prepared. The First-Strand DNA thus prepared was subjected to detection of the human G3PDH and SCGF genes using Taq Polymerase (TaKaRa), the prepared First-Strand DNA as a template, and oligo DNA having base sequences of SEQ. ID Nos. 8 and 9, and SEQ ID Nos. 10 and 11 as primers. As a result, although he SCGF expression was not detected for a single healthy individual, SCGF expression was detected in 1 out of 2 cases for acute lymphocytic leukemia (ALL) and 2 out of 2 cases for acute myeloid leukemia (AML) under the conditions where detected levels of G3PDH were almost equal.

INDUSTRIAL APPLICABILITY

The present invention provides a method of diagnosing leukemia, pre-leukemia or aleukemic malignant blood diseases, a method of diagnosing delayed engraftment of the hematopoietic stem cells after transplantation of the hematopoietic stem cells and graft versus host disease, and a therapeutic agent and a diagnostic kit for these, with the use of antibodies reacting with SCGF.

The invention claimed is:

1. A method for diagnosing leukemia, pre-leukemia or aleukemic malignant blood diseases wherein stem cell growth factor (SCGF) in an in-vivo sample is quantified, wherein the method comprises:
   obtaining an in-vivo patient sample from a patient suspected of having leukemia, pre-leukemia or aleukemic malignant blood disease;
   contacting the patient sample with one or more anti-SCGF antibodies;
   detecting and/or quantifying SCGF present in the patient sample in an immunological assay; thereby obtaining a patient sample SCGF value;
   comparing the patient sample SCGF value to a SCGF cut-off value; wherein the SCGF cut-off value is set based on one or more individuals that do not have leukemia, pre-leukemia, or alenkemic malignant blood disease; and
   diagnosing leukemia, pre-leukemia or aleukemic malignant blood disease if the patient sample SCGF value is above the SCGF cut-off value;
   wherein the leukemia is acute lymphocytic leukemia (ALL), acute mycloid leukemia (AML), or chronic myeloid leukemia (CML), and the pre-leukemia is myelodysplastic syndrome (MDS), and the aleukemic malignant blood disease is non-Hodgkin's lymphoma (NHL) or multiple mycloma (MM).

2. The method according to claim 1, wherein the immunological assay is a sandwich assay.

3. The method according to claim 2, wherein two different anti-SCGF antibodies are used in the sandwich assay, wherein the two different anti-SCGF antibodies react with different epitopes of stem cell growth factor (SCGF).

4. The method according to claim 3, wherein the antibodies are selected from polyclonal and monoclonal antibodies.

5. The method according to claim 4, wherein at least one of the antibodies is a monoclonal antibody, and wherein the at least one monoclonal antibody is selected from a monoclonal antibody recognizing the region shown by the amino acid sequence of residues 6-28 of SEQ. ID No. 1, a monoclonal antibody recognizing the region shown by the amino acid sequence of residues 29-59 of SEQ. ID No. 1, and a monoclonal antibody recognizing the region shown by the amino acid sequence of residues 60-302 of SEQ. ID No. 1.

6. The method of claim 1, wherein the SCGF cut-off value is set by
   obtaining one or more in-vivo normal samples from one or more individuals that do not have leukemia, pre-leukemia, or aleukemic malignant blood disease;
   contacting the one or more normal samples with one or more anti-SCGF antibodies;
   detecting and/or quantifying SCGF present in the one or more normal samples in an immunological assay; thereby obtaining one or more normal sample SCGF values; and
   setting the SCGF cut-off value based on the one or more normal sample SCGF values.

7. The method of claim 1, wherein the in-vivo sample is selected from blood, urine, spinal fluid, and puncture fluid.

8. The method of claim 7, wherein the in-vivo sample is blood, and the blood is selected from whole blood, plasma, and serum.

9. The method of claim 1, wherein the SCGF cut-off value is 18.2 ng/ml.

10. The method of claim 1, wherein the SCGF cut-off value is 15.0 ng/ml.

11. The method of claim 1, wherein the SCGF cut-off value is 13.0 ng/ml.

12. The method of claim 5, wherein the at least one monoclonal antibody is a monoclonal antibody recognizing the region shown by the amino acid sequence of residues 6-28 of SEQ. ID No. 1, wherein the monoclonal antibody is KM2142 produced by hybridoma FERM BP-7922.

13. The method of claim 5, wherein the at least one monoclonal antibody is a monoclonal antibody recognizing the region shown by the amino acid sequence of residues 29-59 of SEQ. ID No. 1, wherein the monoclonal antibody is KM2804 produced by hybridoma FERM BP-7923.

14. The method of claim 5, wherein the at least one monoclonal antibody is a monoclonal antibody recognizing the region shown by the amino acid sequence of residues 60-302 of SEQ. ID No. 1, wherein the monoclonal antibody is KM2945 produced by hybridoma FERM BP-7924.

* * * * *